US012090165B2

(12) United States Patent
Ormandy et al.

(10) Patent No.: US 12,090,165 B2
(45) Date of Patent: Sep. 17, 2024

(54) METHODS FOR REDUCING OR SHUTTING DOWN LACTATION IN NON-HUMAN MAMMALS AND REAGENTS THEREFOR

(71) Applicant: MAMMBIO PTY LTD, Bronte (AU)

(72) Inventors: Chris Ormandy, Darlinghurst (AU);
Samantha Oakes, Darlinghurst (AU);
Nelson Horseman, Cincinnati, OH (US)

(73) Assignee: MAMMBIO PTY LTD, Bronte (AU)

( * ) Notice: Subject to any disclaimer, the term of this patent is extended or adjusted under 35 U.S.C. 154(b) by 733 days.

(21) Appl. No.: 16/646,246

(22) PCT Filed: Sep. 12, 2018

(86) PCT No.: PCT/AU2018/050986
§ 371 (c)(1),
(2) Date: Mar. 11, 2020

(87) PCT Pub. No.: WO2019/051540
PCT Pub. Date: Mar. 21, 2019

(65) Prior Publication Data
US 2020/0206254 A1 Jul. 2, 2020

Related U.S. Application Data

(60) Provisional application No. 62/557,280, filed on Sep. 12, 2017.

(51) Int. Cl.
*A61K 31/713* (2006.01)
*A61K 38/21* (2006.01)
*A61K 45/06* (2006.01)
*A61P 15/14* (2006.01)
*A61P 31/04* (2006.01)

(52) U.S. Cl.
CPC ............ *A61K 31/713* (2013.01); *A61K 38/21* (2013.01); *A61K 45/06* (2013.01); *A61P 15/14* (2018.01); *A61P 31/04* (2018.01)

(58) Field of Classification Search
CPC ...... A61K 38/21; A61K 45/00; A61K 31/713; A61K 38/43; A61K 31/7084; A61K 2039/552; A61P 15/14
See application file for complete search history.

(56) References Cited

U.S. PATENT DOCUMENTS

| 2009/0087454 | A1* | 4/2009 | Salazar | ............ A61K 9/0014 514/44 R |
| 2014/0088032 | A1* | 3/2014 | Ilg | ............ A61P 31/04 514/39 |

FOREIGN PATENT DOCUMENTS

| DE | 2650608 A1 | 5/1977 | |
| EP | 0428876 A2 | 5/1991 | |
| EP | 0428876 A3 | 5/1991 | |
| EP | 1944037 A1 * | 7/2008 | ............ A61K 38/21 |
| WO | 2007/137427 A1 | 12/2007 | |
| WO | 2009/072767 A2 | 6/2009 | |
| WO | 2012152898 A1 | 11/2012 | |

OTHER PUBLICATIONS

Quiroga et al. J Dairy Sci. Oct. 1993;76(10):2913-24 (Year: 1993).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Whisstock et al. Quarterly Reviews in Biophysics. 36(3):307-340, 2007 (Year: 2007).*
Zhu et al. CpG-ODN enhances mammary gland defense during mastitis induced by *Escherichia coli* infection in goats. Vet Immunol Immunopathol. Dec. 15, 2007;120(3-4):168-76 (Year: 2007).*
Martins et al. Vaccine adjuvant uses of poly-IC and derivatives. Expert Rev. Vaccines14(3), 447-459 (2015) (Year: 2015).*
Quiroga et al. Histologic response of the heifer mammary gland to intramammary infusion of interleukin-2 and interferon-gamma. J Dairy Sci. Oct. 1993;76(10):2913-24 (Year: 1993).*
Ning et al. "Effects of continuous low dose infusion of lipopolysaccharide on inflammatory responses, milk production and milk quality in dairy cows", J Anim Physiol Anim Nutr. 102(1): e262-e269 (2017).
International Preliminary Report on Patentability and Written Opinion of the International Searching Authority. Issued in International Application No. PCT/AU2018/050986 dated Mar. 17, 2020. 7 pages.
Sauber et al., "Effect of level of chronic immune system activation on the lactational performance of sows", J. Anim. Sci., 77(8): 1985-1993 (1999).
Zhu et al., "CpG-ODN enhances mammary gland defence mastitis induced by *Escherichia coli* infection in goats", Veterinary Immunology and Immunopathology, 120:168-176 (2007).
Oakes et al., "A mutation in the viral sensor 2'-5'-oligoadenylate synthase 2 causes failure of lactation", PLOS Genetics 13(11): e1007072, 24 pgs (2017).
Petzl et al., "Lipopolysaccharide pretreatment of the udder protects against experimental *Escherichia coli* mastitis", Innate Immunity, 18(3): 467-477 (2011).

* cited by examiner

*Primary Examiner* — Vanessa L. Ford
*Assistant Examiner* — Sandra Dillahunt
(74) *Attorney, Agent, or Firm* — NIXON PEABODY LLP; David S. Resnick; Jeanne Jodoin

(57) ABSTRACT

The disclosure relates generally to methods and reagents for reducing or shutting down lactation in a non-human mammalian subject. In particular, the disclosure relates to a method of reducing or shutting down lactation in a non-human mammalian subject by administering to the subject by intramammary infusion an agent which activate the OAS2 signalling pathway or induce expression of OAS2. In some examples, the methods and reagents of the disclosure may be useful for the prevention of mastitis in a non-human mammalian subject, such as a dairy cow.

10 Claims, 29 Drawing Sheets

Specification includes a Sequence Listing.

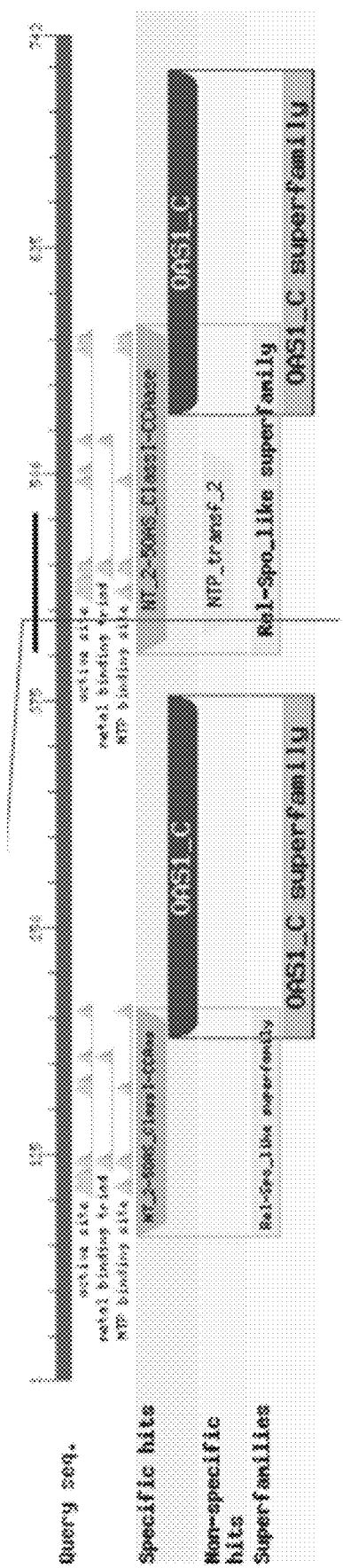
Figure 3, continued

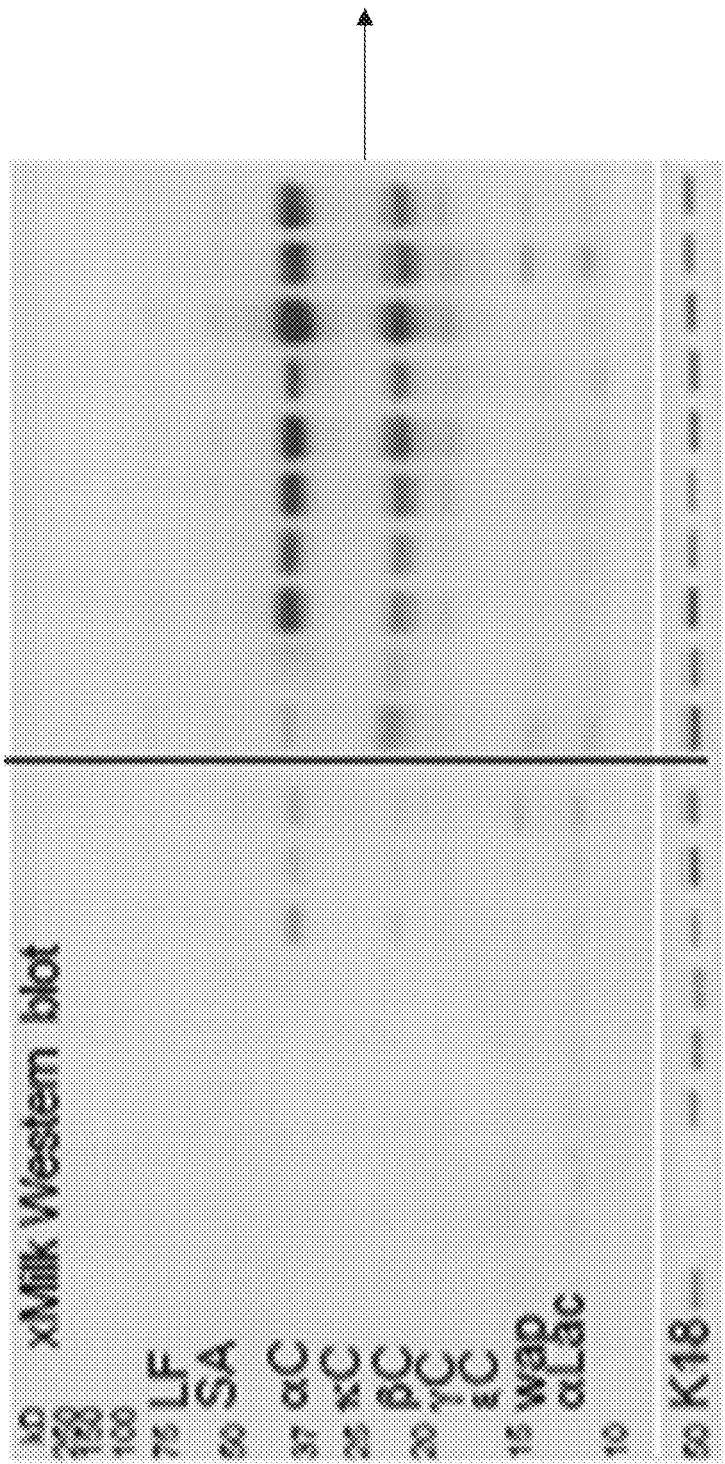
Figure 6, continued

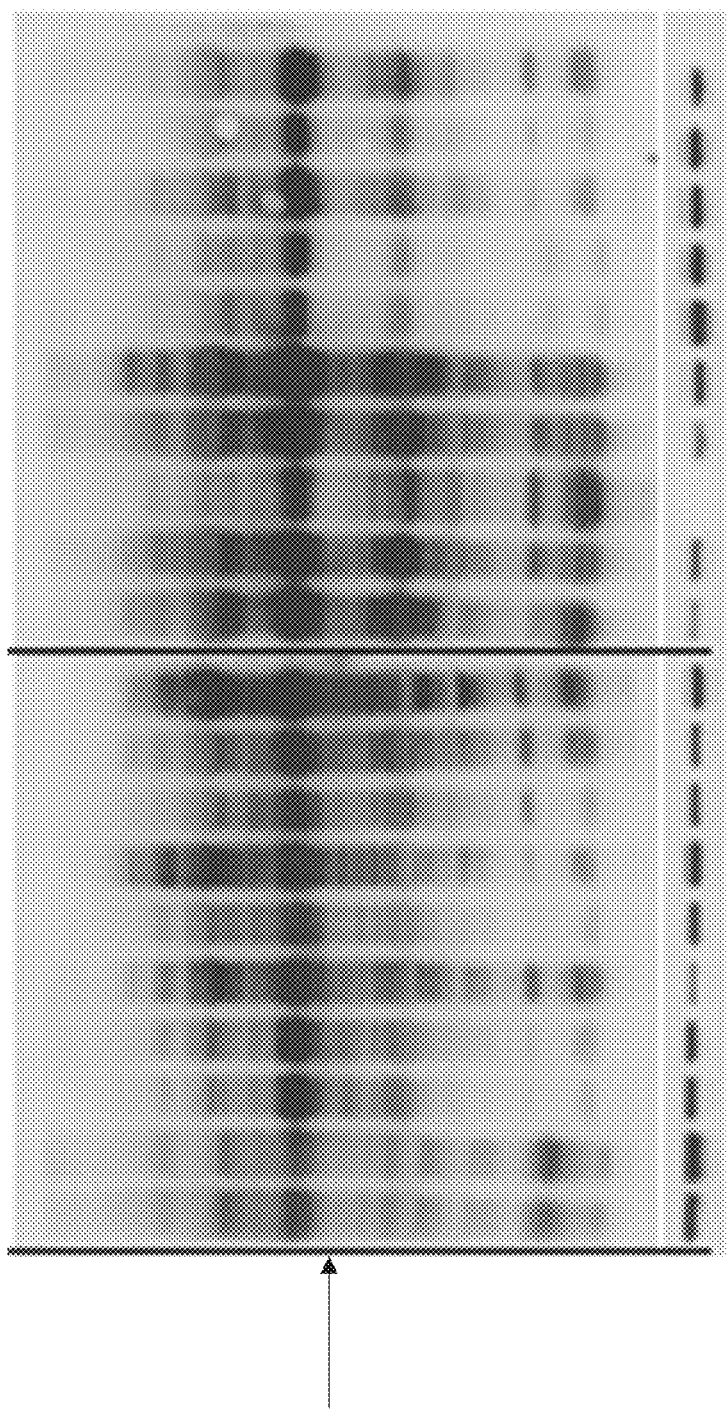
Figure 6, continued

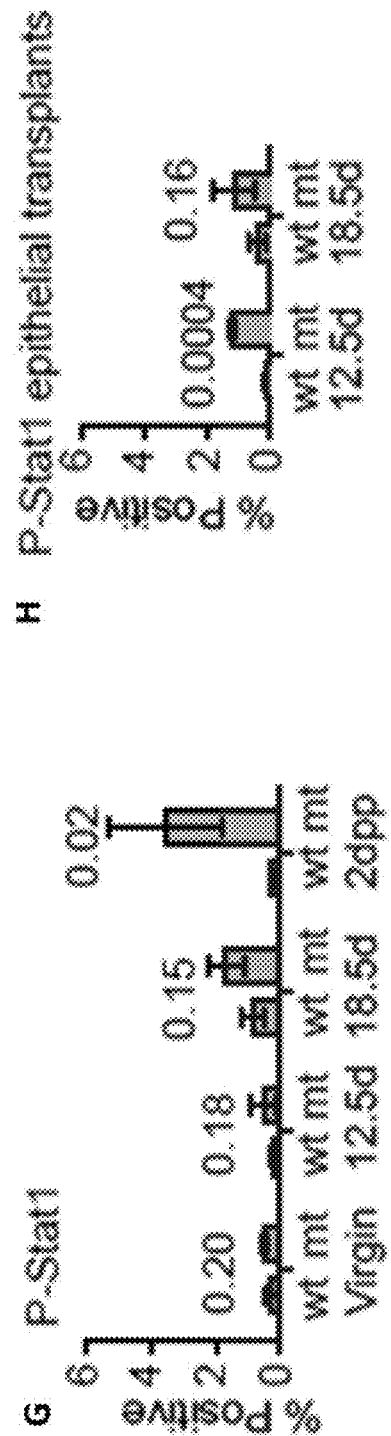
Figure 9, continued

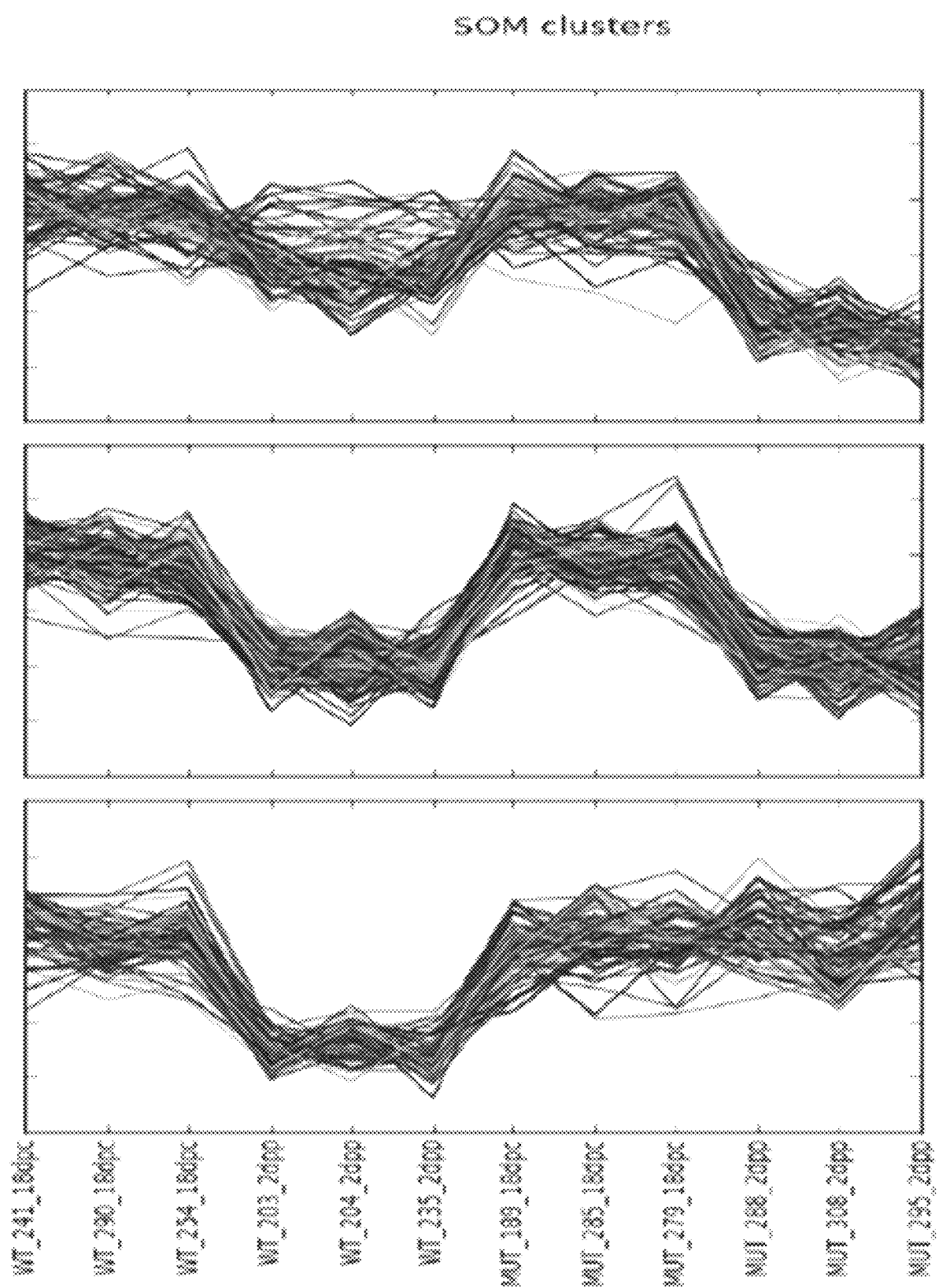
Figure 11A, continued

| | G1 | score | | G2 | score |
|---|---|---|---|---|---|
| DAVID | GO:0003735~structural constituents of ribosome | 4.843 | | mmu03010:Ribosome | 2.823 |
| | GO:0044421~extracellular region part | 0.195 | | PP00C10:EGF-like | 1.304 |
| | transmembrane protein | 0.145 | | mmu04510:Focal adhesion | 0.990 |
| | GO:0005198~molecular binding | 0.053 | | GO:0048666~neuron development | 0.847 |
| | | | | GO:0070161~anchoring junction | 0.611 |
| HALLMARK | No unique sets | | | HALLMARK_MYC_TARGETS_V1 | 0.585 |
| | | | | HALLMARK_PEROXISOME | 0.511 |
| TFT | TTCTNRGAA_V$STAT5B_01 | 0.003 | | V$RF_Q6 | 0.011 |
| | V$FOX_Q2 | 0.008 | | GMTTTTGT_UNKNOWN | 0.011 |
| | V$STAT_01 | 0.008 | | WTGAAAT_UNKNOWN | 0.011 |
| | GGGNKCCATNK_UNKNOWN | 0.012 | | V$GBP_C | 0.055 |
| | YATGNWAAT_V$OCT_C | 0.017 | | CAGCTG_V$AP4_Q5 | 0.055 |
| INVOLUTION & LACTATION | No unique sets | | | No unique sets | |
| PATHWAYS (c2.sp) | REACTOME_FORMATION_OF_THE_TERNARY_COMPLEX_AND_SUBSEQUENTLY_THE_43S_COMPLEX | 0.000 | | REACTOME_SYNTHESIS_SECRETION_AND_DEACYLATION_OF_GHRELIN | 0.000 |
| | REACTOME_ACTIVATION_OF_THE_MRNA_UPON_BINDING_OF_THE_CAP_BINDING_COMPLEX_AND_EIFS_AND_SUBSEQUENT_BINDING_TO_43S | 0.000 | | REACTOME_SMOOTH_MUSCLE_CONTRACTION | 0.001 |
| | KEGG_PPAR_SIGNALING_PATHWAY | 0.000 | | ST_INTEGRIN_SIGNALING_PATHWAY | 0.002 |
| | REACTOME_TRANSCRIPTIONAL_REGULATION_OF_WHITE_ADIPOCYTE_DIFFERENTIATION | 0.000 | | KEGG_VASCULAR_SMOOTH_MUSCLE_CONTRACTION | 0.002 |
| | REACTOME_HORMONE_SENSITIVE_LIPASE_HSL_MEDIATED_TRIACYLGLYCEROL_HYDROLYSIS | 0.004 | | REACTOME_MUSCLE_CONTRACTION | 0.004 |

Figure 11B, continued

| | | |
|---|---|---|
| DAVID | GO:0006614 ribosome<br>GO:0006270 zinc ion binding<br>signal peptide | 4.592<br>0.140<br>0.133 |
| HALLMARK | | No unique sets |
| TFT | | No unique sets |
| INVOLUTION & LACTATION | | No unique sets |
| PATHWAYS (C2.cgp) | | No unique sets |

| | | |
|---|---|---|
| DAVID | GO:0008219 cell death<br>GO:0045087 innate immune response<br>GO:0048870 cell motility<br>GO:0042325 regulation of phosphorylation<br>ubl conjugation pathway | 2.516<br>1.716<br>1.551<br>1.344<br>0.885 |
| HALLMARK | HALLMARK_INTERFERON_GAMMA_RESPONSE<br>HALLMARK_TNFA_SIGNALING_VIA_NFKB<br>HALLMARK_INFLAMMATORY_RESPONSE<br>HALLMARK_IL6_JAK_STAT3_SIGNALING | 0.000<br>0.000<br>0.001<br>0.027 |
| TFT | V$IRF7_01<br>V$IRF_Q6 | 0.000<br>0.013 |
| INVOLUTION & LACTATION | STEIN_2004_INVOLUTION_MOA_IMMUNOGLOBULIN_GENES_UP | 0.000 |
| PATHWAYS (C2.cgp) | REACTOME_IMMUNE_SYSTEM<br>REACTOME_INTERFERON_ALPHA_BETA_SIGNALING<br>REACTOME_CYTOKINE_SIGNALING_IN_IMMUNE_SYSTEM<br>REACTOME_INTERFERON_SIGNALING<br>REACTOME_NEGATIVE_REGULATORS_OF_RIG_I_MDA5_SIGNALING | 0.000<br>0.000<br>0.000<br>0.000<br>0.001 |

Figure 11B, continued

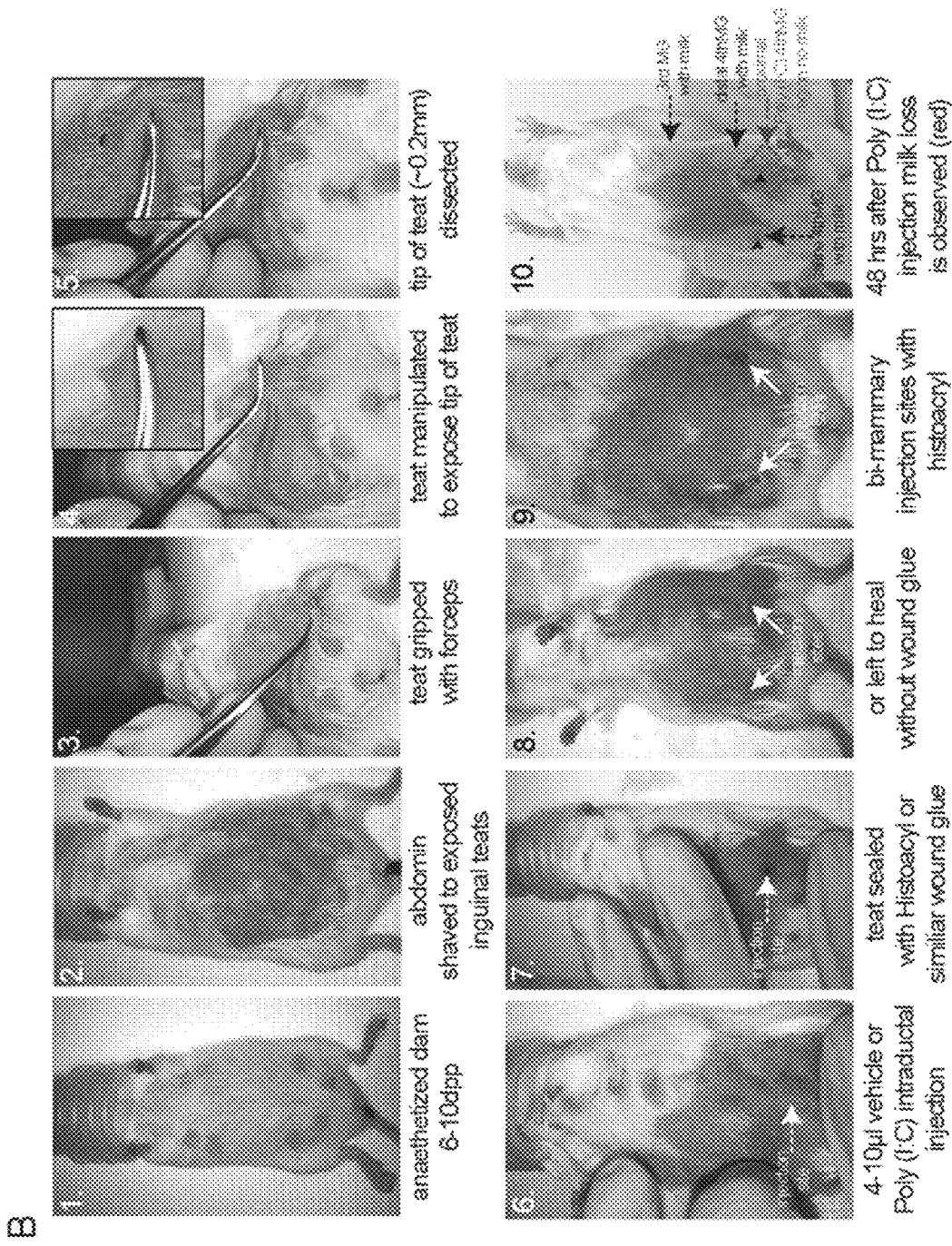
Figure 12, continued

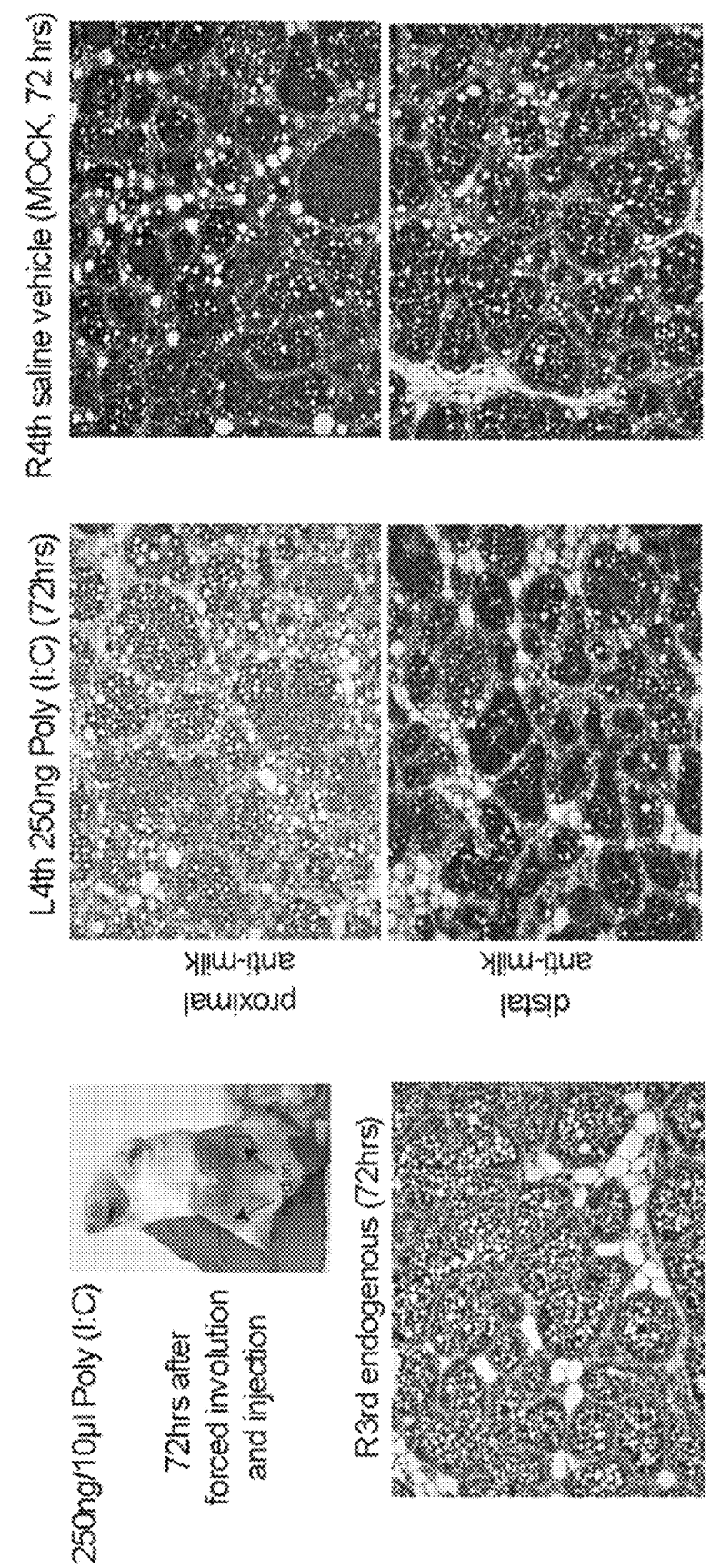
Figure 13, continued

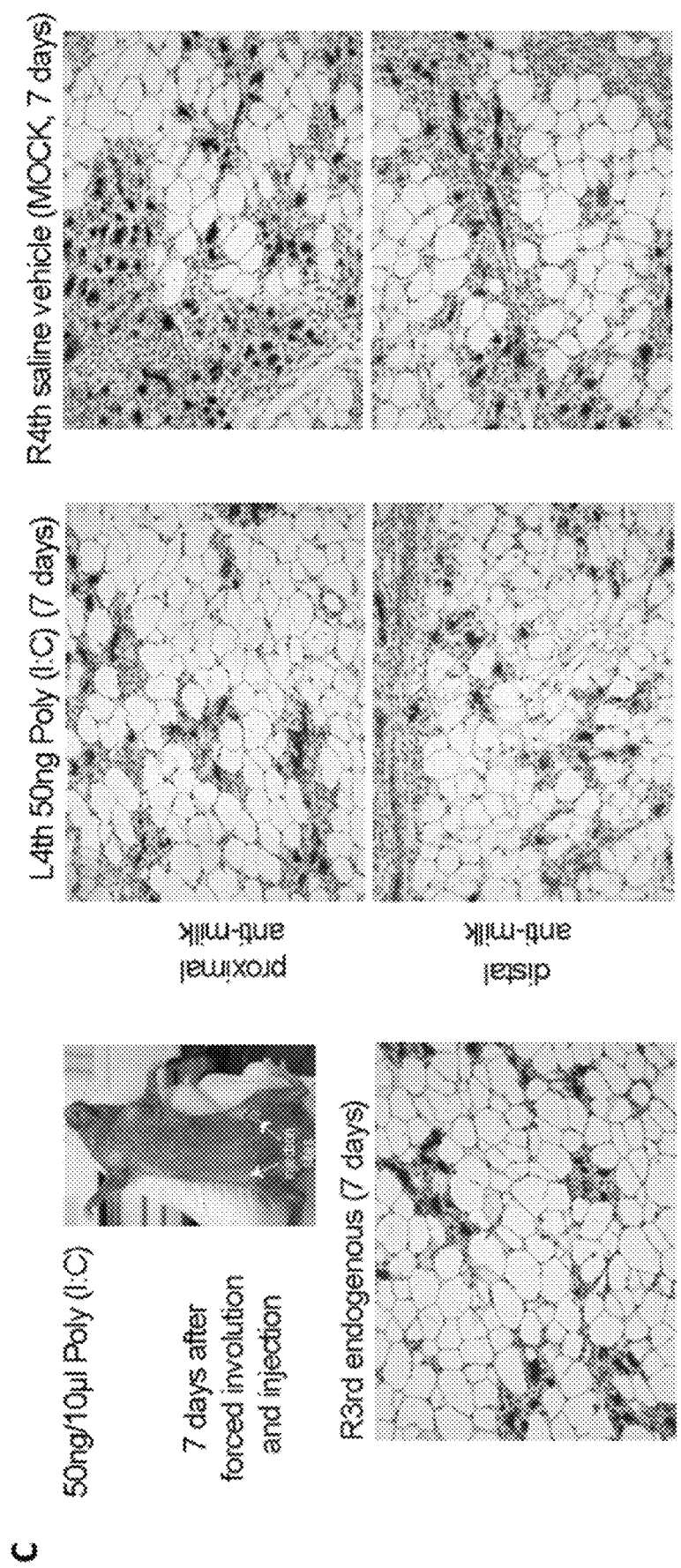
Figure 13, continued

SEQUENCE LISTING

```
<160> NUMBER OF SEQ ID NOS: 3

<210> SEQ ID NO 1
<211> LENGTH: 18
<212> TYPE: DNA
<213> ORGANISM: Mus musculus

<400> SEQUENCE: 1
gctcttccta aagcagat                                                   18

<210> SEQ ID NO 2
<211> LENGTH: 18
<212> TYPE: DNA
<213> ORGANISM: Mus musculus

<400> SEQUENCE: 2
gctcttccta aagcagaa                                                   18

<210> SEQ ID NO 3
<211> LENGTH: 24
<212> TYPE: DNA
<213> ORGANISM: mus musculus

<400> SEQUENCE: 3
ggtgtcagaa ttcaagaagc agac                                            24
```

METHODS FOR REDUCING OR SHUTTING DOWN LACTATION IN NON-HUMAN MAMMALS AND REAGENTS THEREFOR

CROSS-REFERENCE TO RELATED APPLICATIONS

This Application is a U.S. National Phase Entry of International Patent Application No. PCT/AU2018/050986 filed on Sep. 12, 2018, which claims the benefit under 35 U.S.C. § 119(e) of U.S. Provisional Application Ser. No. 62/557,280 filed on filed Sep. 12, 2017, the contents of which are incorporated herein in their entirety by reference.

SEQUENCE LISTING

The instant application contains a Sequence Listing which has been submitted electronically in ASCII format and is hereby incorporated by reference in its entirety. Said ASCII copy, created on Mar. 9, 2020, is named 170231PCT_Sequence_Listing_ST25.txt and is 770 bytes in size.

TECHNICAL FIELD

The present disclosure relates generally to methods and reagents for reducing or shutting down lactation in a non-human mammalian subject. In particular, the present disclosure relates to a method of reducing or shutting down lactation in a non-human mammalian subject by administering to the subject by intramammary infusion an agent which activates the OAS2 signalling pathway or which induces expression of OAS2. In some examples, the methods and reagents of the disclosure may be useful for the prevention of mastitis in a non-human mammalian subject.

BACKGROUND

Mastitis (inflammation of the mammary gland or udder) is a common and serious problem, especially in the dairy industry. Predisposition to Bovine mastitis may be produced by several types of injury and physical trauma, chemical irritantsis or inflamation associated with engorgment of the udder during weaning, and it quickly progresses due to bacterial intramammary infection as a result of the introduction of bacterial pathogens. Mastitis has a high prevalence (up to 50%) and is caused by a variety of gram-positive bacteria such as *Staphylococcus aureus* or *Streptococcus uberis*, gram-negative bacteria such as *Escherichia coli* or *Klebsiella pneumoniae*, and *Mycoplasma* (such as *M. bovis*).

Mastitis causes compositional changes in milk, including an increase in somatic cell count (SCC). Milk from normal (uninfected) cows generally contain below 200,000 somatic cells/ml. An elevation in SCC, above 300,000 somatic cells/ml is abnormal and is an indication of inflammation of the udder. The types of somatic cells present in the milk change to mostly white blood cells, which add many proteolytic and lipolytic enzymes to milk. In addition, more blood serum leaks into the milk than usual. Dairy product quality defects resulting from mastitis are due to enzymatic breakdown of milk protein and fat. Casein, the major milk protein of high nutritional quality, declines and lower quality whey proteins increase which adversely impacts dairy product quality, such as cheese yield, flavor and quality. Protein breakdown in the milk can occur in milk from cows with clinical or subclinical mastitis due to the presence of proteolytic enzymes. Plasmin increases proteolytic activity more than 2-fold during mastitis. Plasmin and enzymes derived from somatic cells can cause damage to casein in the udder before milk removal. Deterioration of the milk protein may also continue during processing and storage of milk from infected cows. Other compositional changes in the milk include a decrease in potassium and calcium levels.

Mastitis is the single most costly disease in the dairy industry, and costs the US dairy industry about US$2 billion annually or 11% of the total US milk production. The cost includes reduced milk production, discarded milk, replacement cows, medication, labor, and veterinary services.

Currently, mastitis is treated with antibiotics, antiinflammatories and oxytocin. These treatments, however, are often time consuming (sometimes several successive intramammary applications), expensive, and not fully efficacious.

Rather than treat mastitis, it would be preferable to reduce the incidence of or prevent mastitis. Whilst the incidence of mastitis can be reduced through the use of, for example, pre-milking germicidal teat dips, no products are universally effective for preventing mastitis. As such, there is a need for further and more effective preventative products and practices for reducing the incidence of mastitis in the dairy industry.

SUMMARY

Using N-ethyl-N-nitrosourea (ENU) mutagenesis and a forward genetic screen for failed lactation, the present inventors established a mouse line in which heterozygous dams showed partial penetrance of poor lactation, producing litters that failed to thrive, and homozygous dams experienced complete failure of lactation, providing a dominant pattern of inheritance. The inventors were also able to identify a non-synonymous mutation in OAS2 (1405N) in a conserved region of the OAS2 catalytic domain which caused lactation failure and milk stasis in the mutated mice.

In further experiments characterising the mouse model for failed lactation, the inventors demonstrated that the OAS2 mutation caused activation of OAS2 driven signalling to prevent the complete activation of lactation in the post-partum period. The effect of the mutation could be detected via Stat1 activation from mid pregnancy and mammary epithelial transplants showed that the effect was mammary cell autonomous as the mutation was only required in the mammary epithelial cells for effect. The inventors found that stimulation of the OAS2 pathway can produce a persistent interferon response and reduced activation of STAT5, which is essential for activation of milk secretion during the post-partum period. On this basis, the inventors concluded that the OAS2 pathway was involved in pathogenesis of lactation failure and milk stasis, and that OAS2 activators may therefore be used to reduce or shut down lactation.

To test this, the inventors performed animal experiments in which a representative OAS2 activator, the viral mimetic, Poly (I:C), was administered to the mammary glands of lactating mice by intramammary infusion. By doing so, the inventors were able to show for the first time that an OAS2 activator can be used to reduce or shut down lactation when administered to a lactating animal by intramammary infusion via the teat and main mammary duct/sinus. Importantly, the administration of the OAS2 activator resulted in cessation of milk production, precocious involution of the mammary epithelium and mammary tissue remodelling so that the alveolar structures condense. Importantly the regions of the mammary gland that have stopped producing milk due to infusion of the OAS2 activator can recover and become fully capable of lactation after a subsequent pregnancy, demonstrating that the effect of the OAS2 activator is not permanent.

Given the importance of mastitis in the dairy industry, the inventors performed similar experiments in a herd of dairy cows and were able to show that intramammary infusion of poly I:C into the udders of Holstein dairy cows causes transient immunostimulation and suppressed lactation without undesirable side effects.

Thus, the present disclosure provides a method of reducing or shutting down lactation in a non-human mammalian subject, said method comprising administering to the mammary gland of the subject an agent which activates the OAS2 signalling pathway or induces expression of OAS2 in the mammary gland of the subject.

In one example, the agent which activates the OAS2 signalling pathway or induces expression of OAS2 is interferon or an interferon inducing agent. For example, the method may comprise administering interferon to the mammary gland of the subject. For example, the method may comprise administering an interferon inducing agent to the mammary gland of the subject.

In one example, the interferon inducing agent which activates the OAS2 signalling pathway or induces expression of OAS2 is a toll-like receptor (TLR) agonist. For example, the TLR agonist may be selected from the group consisting of: polyinosinic-polycytidylic acid (Poly (I:C)) or a derivative thereof selected from polyI:polyC(12)U and polyinosinic-polycytidylic acid stabilized with poly-L-lysine and carboxymethylcellulose (Poly-ICLC); polyadenylic-polyuridylic acid (poly A:U), bacterial lipopolysaccharide (LPS); monophosphoryl lipid A (MPL); a CpG dinucleotide (CpG-ODN); bacterial flagellin protein; and profilin protein. In one particular example, the agent which activates the OAS2 signalling pathway or induces expression of OAS2 in the mammary gland is Poly (I:C) or a derivative thereof e.g., selected from polyI:polyC(12)U and polyinosinic-polycytidylic acid stabilized with poly-L-lysine and carboxymethylcellulose (Poly-ICLC).

In one example, the agent which activates the OAS2 signalling pathway or induces expression of OAS2 in the mammary gland is Poly (I:C). The TLR agonist may be administered to the mammary gland in a dose of at least about 1 mg. For example, the TLR agonist may be administered to the mammary gland in a dose of at least about 1 mg to about 50 mg. For example, the TLR agonist may be administered to the mammary gland in a dose of at least about 1 mg to about 10 mg. In one particular example, the TLR agonist is Poly (I:C) which is administered to the mammary gland at a dose of about 1 mg to about 50 mg. In another example, the Poly (I:C) is administered to the mammary gland at a dose of about 1 mg to about 10 mg. For example, the Poly (I:C) may be is administered to the mammary gland at a dose of about 1 mg. For example, the Poly (I:C) may be is administered to the mammary gland at a dose of about 2 mg. For example, the Poly (I:C) may be is administered to the mammary gland at a dose of about 3 mg. For example, the Poly (I:C) may be is administered to the mammary gland at a dose of about 4 mg. For example, the Poly (I:C) may be is administered to the mammary gland at a dose of about 5 mg. For example, the Poly (I:C) may be is administered to the mammary gland at a dose of about 6 mg. For example, the Poly (I:C) may be is administered to the mammary gland at a dose of about 7 mg. For example, the Poly (I:C) may be is administered to the mammary gland at a dose of about 8 mg. For example, the Poly (I:C) may be is administered to the mammary gland at a dose of about 9 mg. For example, the Poly (I:C) may be is administered to the mammary gland at a dose of about 10 mg. In another example, the interferon inducing agent which activates the OAS2 signalling pathway or induces expression of OAS2 is a stimulator of interferon gene (STING, TMEM173) or STING agonist.

In another example, the interferon inducing agent which activates the OAS2 signalling pathway or induces expression of OAS2 is RNase L or an RNase L activator.

In one example, the agent which activates the OAS2 signalling pathway or induces expression of OAS2 in the mammary gland is administered in an amount sufficient to reduce or shut down lactation in a non-human mammalian subject.

According to any of the examples described herein, administration of the agent to the mammary gland of the non-human mammalian subject is by intramammary infusion e.g., intraductal infusion directly into the main mammary sinus or galactophore.

In one example, the method comprises administering a single dose of the agent to the non-human mammalian subject to thereby reduce or shut down lactation.

In another example, the method comprises administering repeat doses of the agent until lactation is reduced or shut down. For example, the agent may be administered to the non-human mammalian subject on a daily basis until lactation is reduced or shut down. For example, the agent may be administered to the non-human mammalian subject every second day until lactation is reduced or shut down. For example, the agent may be administered to the non-human mammalian subject every third day until lactation is reduced or shut down. For example, the agent may be administered to the non-human mammalian subject on a weekly basis until lactation is reduced or shut down.

In one example, reducing or shutting down lactation in the subject e.g., by performing a method as described herein, prevents mastitis in the non-human mammalian subject. In accordance with this example, the agent which activates the OAS2 signalling pathway or induces expression of OAS2 in the mammary gland is capable of preventing mastitis in the non-human mammalian subject in the absence of an antimicrobial agent being administered. Accordingly, in one example, the method of the disclosure does not comprise administering an antimicrobial agent to the non-human mammalian subject. That is, the method may comprise administering an agent which activates the OAS2 signalling pathway or induces expression of OAS2 and not administering an antimicrobial agent to the non-human mammalian subject. In one example, the method of the disclosure consists essentially of administering to the mammary gland of the non-human mammalian subject by intramammary infusion an agent which activates the OAS2 signalling pathway or induces expression of OAS2 in the mammary gland of the subject.

In an alternative example, the method of the disclosure further comprises administering to the non-human mammalian subject an antimicrobial agent e.g., by intramammary infusion, to prevent microbial infection in the mammary gland of the subject. In accordance with this example, the antimicrobial agent is administered as a preventative or prophylactic agent against microbial infection e.g., bacterial infection, in the mammary gland, whereas the agent which activates the OAS2 signalling pathway or induces expression of OAS2 is administered for the purpose of reducing or shutting down lactation in the non-human mammalian subject. In one example, the antimicrobial agent and the agent which activates the OAS2 signalling pathway or induces expression of OAS2 in the mammary gland may be administered separately e.g., sequentially. In another example, the antimicrobial agent may be administered together with the agent which activates the OAS2 signalling pathway or induces expression of OAS2 in the mammary gland e.g., in the same formulation.

In one example, the method of the disclosure does not comprise administering to the non-human mammalian subject an additional agent which shuts down or reduces lactation.

In another example, the method of the disclosure further comprises administering to the non-human mammalian subject a further agent which shuts down or reduces lactation. In one example, the further agent which shuts down or reduces lactation and the agent which activates the OAS2 signalling pathway or induces expression of OAS2 in the mammary gland may be administered separately e.g., sequentially. In another example, the further agent which shuts down or reduces lactation may be administered together with the agent which activates the OAS2 signalling pathway or induces expression of OAS2 in the mammary gland e.g., in the same formulation.

In one example, the non-human mammalian subject with whom the method of the disclosure may be performed is a livestock animal e.g., such as a ruminant animal used in the production of milk for human consumption. For example, the non-human mammalian subject may be a dairy cow.

In one example, the non-human mammalian subject with whom the method of the disclosure may be performed is a companion animal. For example, the companion animal may be selected from the group consisting of a cat, a dog, a horse, a rodent and a rabbit.

In one example, the non-human mammalian subject with whom the method of the disclosure may be performed is a working animal. For example, the working animal may be selected from the group consisting of a horse, a dog, a mule, a donkey, a camel, oxen and a pig.

In one example, the non-human mammalian subject with whom the method of the disclosure may be performed is a sporting animal. For example, the sporting animal may be a horse or a dog.

In any one or more of the foregoing example, the non-human mammalian subject with whom the method of the disclosure is performed is lactating, but is not suffering from mastitis.

Alternatively, the non-human mammalian subject with whom the method of the disclosure is performed is lactating and suffering from mastitis. In accordance with this example, the method of the disclosure shuts down or reduces lactation in the non-human mammalian subject suffering from mastitis.

The present disclosure also provide a method of preventing mastitis in a non-human mammalian subject which is lactating and not suffering from mastitis, comprising reducing or shutting down lactation in the non-human mammalian subject by performing a method of reducing or shutting down lactation as described herein.

The present disclosure also provide an intramammary veterinary composition comprising an agent which activates the OAS2 signalling pathway or induces expression of OAS2 in the mammary gland of a non-human mammalian subject and a pharmaceutically acceptable excipient or carrier, wherein the agent is present in an amount sufficient to reduce or shut down lactation in the non-human mammalian subject.

In one example of the intramammary veterinary composition, the agent which activates the OAS2 signalling pathway or induces expression of OAS2 is interferon or an interferon inducing agent. In one example, the agent which activates the OAS2 signalling pathway or induces expression of OAS2 is interferon. In one example, the agent which activates the OAS2 signalling pathway or induces expression of OAS2 is an interferon inducing agent.

In one example of the intramammary veterinary composition, the interferon inducing agent which activates the OAS2 signalling pathway or induces expression of OAS2 is a TLR agonist. For example, the TLR agonist may be selected from the group consisting of: polyinosinic-polycytidylic acid (Poly (I:C)) or a derivative thereof selected from polyI:polyC(12)U and polyinosinic-polycytidylic acid stabilized with poly-L-lysine and carboxymethylcellulose (Poly-ICLC); polyadenylic-polyuridylic acid (poly A:U), bacterial lipopolysaccharide (LPS); monophosphoryl lipid A (MPL); a CpG dinucleotide (CpG-ODN); bacterial flagellin protein; and profilin protein. In one particular example, the agent which activates the OAS2 signalling pathway or induces expression of OAS2 in the mammary gland is Poly (I:C) or a derivative thereof e.g., selected from polyI:polyC (12)U and polyinosinic-polycytidylic acid stabilized with poly-L-lysine and carboxymethylcellulose (Poly-ICLC). In one example, the agent which activates the OAS2 signalling pathway or induces expression of OAS2 in the mammary gland is Poly (I:C). The TLR agonist may be administered to the mammary gland in a dose of at least about 1 mg. For example, the TLR agonist may be administered to the mammary gland in a dose of at least about 1 mg to about 50 mg. For example, the TLR agonist may be administered to the mammary gland in a dose of at least about 1 mg to about 10 mg. In one particular example, the TLR agonist is Poly (I:C) which is administered to the mammary gland at a dose of about 1 mg to about 50 mg. In another example, the Poly (I:C) is administered to the mammary gland at a dose of about 1 mg to about 10 mg. For example, the Poly (I:C) may be is administered to the mammary gland at a dose of about 1 mg. For example, the Poly (I:C) may be is administered to the mammary gland at a dose of about 2 mg. For example, the Poly (I:C) may be is administered to the mammary gland at a dose of about 3 mg. For example, the Poly (I:C) may be is administered to the mammary gland at a dose of about 4 mg. For example, the Poly (I:C) may be is administered to the mammary gland at a dose of about 5 mg. For example, the Poly (I:C) may be is administered to the mammary gland at a dose of about 6 mg. For example, the Poly (I:C) may be is administered to the mammary gland at a dose of about 7 mg. For example, the Poly (I:C) may be is administered to the mammary gland at a dose of about 8 mg. For example, the Poly (I:C) may be is administered to the mammary gland at a dose of about 9 mg. For example, the Poly (I:C) may be is administered to the mammary gland at a dose of about 10 mg.

In one example of the intramammary veterinary composition, the interferon inducing agent which activates the OAS2 signalling pathway or induces expression of OAS2 is a stimulator of interferon gene (STING) or STING agonist.

In another example of the intramammary veterinary composition, the interferon inducing agent which activates the OAS2 signalling pathway or induces expression of OAS2 is RNase L or an RNase L activator.

In one example of the intramammary veterinary composition, the agent which activates the OAS2 signalling pathway or induces expression of OAS2 in the mammary gland is present in an amount sufficient to reduce or shut down lactation in a non-human mammalian subject. For example, the agent which activates the OAS2 signalling pathway or induces expression of OAS2 in the mammary gland is present in an amount sufficient to reduce or shut down lactation in a non-human mammalian subject in the absence of any further active ingredients e.g., such as an antimicrobial agent.

In one example, the intramammary veterinary composition consists essentially of the agent which activates the OAS2 signalling pathway or induces expression of OAS2. In one example, the intramammary veterinary composition does not contain a further active ingredient e.g., such as an antimicrobial agent.

In one example, the intramammary veterinary formulation may further comprise an antimicrobial agent e.g., which is suitable for intramammary infusion, to prevent microbial infection in the mammary gland of a subject to whom the formulation is administered. In accordance with this example, the antimicrobial agent is included in the formulation as a preventative or prophylactic agent against microbial infection e.g., bacterial infection, in the mammary gland, whereas the agent which activates the OAS2 signalling pathway or induces expression of OAS2 is included in the formulation to reduce or shut down lactation in the non-human mammalian subject to whom the formulation is administered.

In yet another example, the veterinary formulation further comprises a further agent which shuts down or reduces lactation i.e., in addition to the agent which activates the OAS2 signalling pathway or induces expression of OAS2 in the mammary gland of a non-human mammalian subject. In one example, the further agent is a serotonin-selective reuptake inhibitor (SSRI).

The present disclosure also provides the intramammary veterinary composition of the disclosure for use in reducing or shutting down lactation in a non-human mammalian subject e.g., according to the method described herein.

The present disclosure also provides the intramammary veterinary composition of the disclosure for use in preventing mastitis in a lactating non-human mammalian subject not suffering from mastitis e.g., according to the method described herein.

In one example, the intramammary veterinary composition is for use in preventing mastitis in a non-human mammalian subject in the absence of an antimicrobial agent.

The present disclosure also provides for the use of an agent which activates the OAS2 signalling pathway or induces expression of OAS2 in the preparation of a medicament for reducing or shutting down lactation in a non-human mammalian subject in need thereof.

The present disclosure also provides for the use of an agent which activates the OAS2 signalling pathway or induces expression of OAS2 in the preparation of a medicament for preventing mastitis in a non-human mammalian subject not suffering from mastitis.

Exemplary agents which activate the OAS2 signalling pathway or induce expression of OAS2 are described herein and shall be taken to apply mutatis mutandis to any other example of the disclosure unless specifically stated otherwise.

The present disclosure also provides a kit for reducing or shutting down lactation in a non-human mammalian subject, said kit comprising:
(i) an intramammary veterinary composition as described herein; and
(ii) instructions for administering the intramammary veterinary composition to a non-human mammalian subject by intramammary infusion e.g., according to the method described herein.

In one example, the kit is for preventing mastitis in a non-human mammalian subject not suffering from mastitis.

In another example, the kit is for reducing or shutting down lactation in a non-human mammalian suffering from mastitis who is in need of drying off.

DETAILED DESCRIPTION

General

Figure 1:
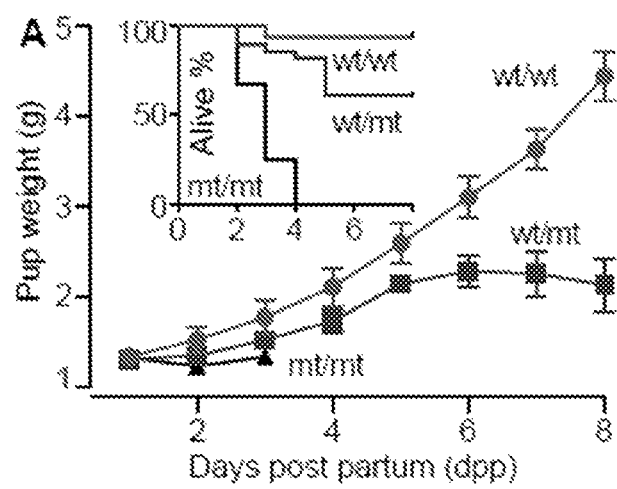
FIG. 1 shows the lactation performance of wildtype (wt/wt), heterozygous mutant (wt/mt) and homozygous mutant (mt/mt) dams assessed by pup weight-gain or survival (inset). Error bars show standard error of the mean for 4-5 litters per genotype of 7 pups each. wt/wt n=35, wt/mt n=28 and mt/mt n=28 pups.

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

The term "about" as used herein refers to a range of +/−10% of the specified value.

Selected Definitions

As used herein, the term "reduce", "reducing" or similar in the context of lactation shall be understood to mean that the milk produced from a lactating non-human mammal administered the agent which activates the OAS2 signalling pathway or induces expression of OAS2, or intramammary veterinary composition comprising same, has a reduced volume of production relative to if the lactating non-human mammal was not administered the agent or intramammary veterinary composition.

As used herein, the term "shutting down lactation", "drying off", or similar terminology, refers to the cessation of milk production in a lactating non-human mammal.

As used herein, the term "mastitis" refers to an inflammation of a mammary gland, a breast or an udder, caused by a physical injury, introduction of chemicals, viruses, fungus, parasites or, most commonly, bacterial invasion and their toxins. "Mastitis" is used to describe all forms of such inflammation, including subclinical and clinical mastitis, clinical mastitis including mild, severe and chronic mastitis.

In sub-clinical mastitis, no swelling of the breast or udder is detected nor are there observable abnormalities in the milk. This type of mastitis is commonly referred to as "subclinical". In livestock animals, especially dairy cows, special screening tests, including the California Mastitis Test (CMT), Wisconsin Mastitis Test (WMT) based on an estimation of somatic cell counts and the catalase test will show changes in the milk composition in case of subclinical mastitis. Clinical mastitis can be mild or acute, and is characterized by the presence of leukocytes in the milk. Mild clinical mastitis involves changes in the milk appearance including presence of flakes or clots, watery milk or other unusual forms of the milk. Mild clinical mastitis may be accompanied by other symptoms including hot, sensitive or swollen breast or udder.

Severe clinical mastitis involves the symptoms of hot, sensitive, firm breast or udder that is quite painful to the lactating subject. The onset of severe clinical mastitis is sudden and the lactating subject may become ill showing signs of fever, rapid pulse, depression, weakness and loss of appetite. When the whole lactation system of the subject is affected, the condition is referred to as acute systemic mastitis. The severe symptoms may be also accompanied with cessation of milk production.

Accordingly, in one example, the terms "prevent mastitis", "prevents mastitis", "preventing mastitis" or similar as used herein, shall refer to performance of the method of the disclosure in a non-human mammalian subject that is lactating and that is, at the time, asymptomatic for mastitis or inflammation of udder tissues in order to prevent or avoid the development of mastitis. According to another example, the terms "prevent mastitis", "prevents mastitis", "preventing mastitis" or similar as used herein, shall refer to performance of the method of the disclosure in a non-human mammalian subject that is lactating and that is, at the time, suffering from subclinical or mild mastitis. In accordance with this latter example, the method of the disclosure may prevent progression of subclinical or mild mastitis to clinical mastitis.

As used herein, the term "non-human mammalian subject" shall be taken in its broadest context to include any non-human mammal which is lactating and for which it desired to reduce or shut down lactation (also referred to as "drying-off") e.g., such as to prevent mastitis, reduce fatigue and/or to wean young. Exemplary non-human mammalian subjects for which the methods, intramammary veterinary compositions and kits of the disclosure may be useful are described herein and include, for example, livestock species, companion animals, working animals, and sport animals.

As used herein, the term "interferon inducing agent" or similar will be understood to mean an agent which induces or stimulates expression of interferon protein(s) and/or induces an interferon response in a subject.

Active Ingredients

The present disclosure provides a method of reducing or shutting down lactation in a non-human mammalian subject, comprising administering to the mammary gland of the non-human mammalian subject an agent which activates the OAS2 signalling pathway or induces expression of OAS2 in the mammary gland of the subject.

The present disclosure also provides an intramammary veterinary composition comprising an agent which activates the OAS2 signalling pathway or induces expression of OAS2 for use in a method of the disclosure, as well as kits comprising same.

In one example, the agent which activates the OAS2 signalling pathway or induces expression of OAS2 is interferon or an interferon inducing agent. For example, the method may comprise administering interferon to the mammary gland of the subject. For example, the method may comprise administering an interferon inducing agent to the mammary gland of the subject.

In one example, the agent which activates the OAS2 signalling pathway or induces expression of OAS2 is toll-like receptor (TLR) agonist. The TLR agonist may be any ligand that is recognized by one of the family of TLRs. TLRs are critical for the innate immune response in mammals.

TLRs are transmembrane glycoproteins, which are expressed in leukocytes and the epithelial cells of mucosal surfaces, and which are composed of extracellular, trans membrane and intracellular signalling domains. The extracellular domains have leucine-rich repeat modules and are responsible for binding distinct ligands that are broadly shared by pathogens, collectively known as pathogen-associated molecular patterns (PAMPs). Upon binding with said ligands activation of the TLR signalling pathway occurs, the initial step being the ligand-induced dimerization of TLRs on the cell membrane (Jin and Lee; (2008) *Immunity,* 29:182-191). There are two major types of TLRs: those that reside in intracellular compartments (in the membrane of endosomes) and which can be activated by viral and bacterial nucleic acids e.g., TLR3, TLR7, TLR8 and TLR9; and those that are expressed on the cell surface and which can be activated by outer membrane components of bacteria, fungi and protozoan organisms e.g., TLR1, TLR2, TLR4, TLR5 and TLR6. Upon TLR activation by an agonistic compound a signalling pathway is triggered culminating in the production of pro-inflammatory mediators, such as chemokine, cytokines and cell adhesion molecules, producing an interferon response and up regulation of OAS2 levels (Kaiwa and Akira, (2007) *Trend. Mol. Med.* 13:460-469).

In one example, the TLR agonist that is useful in the method, intramammary veterinary composition or kit of the present disclosure is recognized by TLR3 and is a viral or synthetic double stranded RNA, such as polyadenylic-polyuridylic acid (poly A:U), polyinosinic-polycytidylic acid (Poly (I:C)) or a derivative of Poly (I:C) selected from polyI:polyC(12)U, and polyinosinic-polycytidylic acid stabilized with poly-L-lysine and carboxymethylcellulose (poly-ICLC). In one example, the TLR agonist is Poly (I:C). In one example, the TLR agonist is polyI:polyC(12)U. In one example, the TLR agonist is poly-ICLC. In one example, the TLR agonist is poly A:U. Other agonists of TLR3 are known in the art and contemplated for used in the method and intramammary veterinary composition of the disclosure.

In another example, the TLR agonist that is useful in the method, intramammary veterinary composition or kit of the present disclosure is a lipoprotein or lipopeptide derivative recognized by TLR2 in complex with TLR1 or TLR6, such as the synthetic triacylated lipopeptide PAM$_3$CSK$_4$ (Jin and Lee; supra), that retains most of the immune stimulatory activity of the full-length lipoproteins, diacylated lipoprotein derivatives, such as fibroblast-stimulating lipopeptide-1 (FSL-1) i.e. Pam$_2$CGDPKHPKSF, derived from *Mycoplasma salivarium*, and macrophage-activating lipopeptide-2 (MALP-2) from *M. fermentans*, i.e. S-[2,3-bispalmitoyloxy-(2R)-propyl]-cysteinyl-SNNDESNISFKEK, yeast zymosan (betaglucan) and lipoteichoic acid. Other agonists of TLR2, TLR1 and/or TLR6 are known in the art and contemplated for used in the method and intramammary veterinary composition of the disclosure.

In another example, the TLR agonist that is useful in the method, intramammary veterinary composition or kit of the present disclosure is a TLR4 agonist which is a lipopolysaccharide (LPS) preparation from a natural or mutant strain of gram-negative bacteria. Alternatively, the TLR4 agonist may be the hydrophobic component of a LPS referred to as lipid A or monophosphyl lipid A (MPLA). Alternatively, the TLR4 agonist may be a synthetic derivative of an LPS as described in Gaekwad et al., (2010) *J. Biol. Chem.* 285: 29375-29386), such as lipid A or Kdo-lipid A from *N. meningitides* and lipid A or Kdo2-lipid A from *E. coli*. In one example, the TLR4 agonist is LPS or Kdo2-lipid A (Re-LPS) of *E. coli*. The advantage of Kdo2-Lipid A over LPS is that it is a reproducible in its production and a more defined natural product, and it can be detected by ESI/MS at the low concentrations used to stimulate animal cells. Other agonists of TLR4 are known in the art and contemplated for used in the method and intramammary veterinary composition of the disclosure.

In another example, the TLR agonist that is useful in the method, intramammary veterinary composition or kit of the present disclosure is a flagellin protein from flagellated gram-positive and gram-negative bacteria, which is recognised by TLR5. Other agonists of TLR5 are known in the art and contemplated for used in the method and intramammary veterinary composition of the disclosure.

In another example, the TLR agonist that is useful in the method, intramammary veterinary composition or kit of the present disclosure is recognized by TRL7 and TLR8. In one example, the agonist of TRL7 and/or TLR8 is a single-stranded RNA. In another example, the agonist of TRL7 and/or TLR8 is a synthetic small molecule agonist, such as an imidazoquinoline (e.g., Resiquimod—R848), imiquimod or a thiazoloquinoline (e.g., CL075). Other agonists of TLR7 and/or 8 are known in the art and contemplated for used in the method and intramammary veterinary composition of the disclosure.

In another example, the TLR agonist that is useful in the method, intramammary veterinary composition or kit of the present disclosure is recognized by TLR9. In one example, the agonist of TLR9 is a microbial DNA or synthetic oligonucleotide derived therefrom, preferentially phosphorothioates (PS) and phosphodiester (PO) oligonucleotides e.g., a CpG oligodeoxynucleotides (CpG ODN). Suitable CpG ODNs which are recognised by TLR9 are known in the art and contemplated for use in the method and intramammary veterinary composition of the disclosure.

In another example, the TLR agonist that is useful in the method, intramammary veterinary composition or kit of the present disclosure is recognized by TLR11. In one example, the agonist of TLR11 is a bacterial flagellin or profilin protein or peptide.

In one example, the agent which activates the OAS2 signalling pathway or induces expression of OAS2 is a stimulator of interferon gene (STING) or STING agonist. For example, the agent which activates the OAS2 signalling pathway or induces expression of OAS2 may be the STING protein. Alternatively, or in addition, the agent which activates the OAS2 signalling pathway or induces expression of OAS2 may be a STING agonist, a number of which are known in the art. For example, an exemplary STING agonist for use in activating the OAS2 signalling pathway or inducing expression of OAS2 may be SB 11285 as described in Challa et al., (2017) *Journal of Clinical Oncology* 35(15): suppl.e14616, the contents of which is incorporated by reference herein. In another example, the STING agonist may be 5,6-dimethylxanthenone-4-acetic acid (DMXAA) as described in Guo et al., (2015) *Antimicrobial Agents for Chemotherapy*, 59(2):1273-1281, the contents of which is incorporated by reference herein. Other STING agonists are known in the art and contemplated for use herein.

In one example, the agent which activates the OAS2 signalling pathway or induces expression of OAS2 is RNase L or an RNase L activator. For example, the agent which activates the OAS2 signalling pathway or induces expression of OAS2 may be RNase L. Alternatively, or in addition, the agent which activates the OAS2 signalling pathway or induces expression of OAS2 may be an RNase L activator, a number of which are known in the art. For example, the RNase L activator may be an activator of RNaseL as described in Thakur et al., (2007) *PNAS*, 104(23):9585-9590, the contents of which is incorporated by reference herein. In another example, the activator of RNase L may be a 2'5'oligoadenylate, as described in Cole et al., (1997) *Journal of Biological Chemistry*, 272:19187-19192, the contents of which is incorporated by reference herein. Other RNase L activators are known in the art and contemplated for use herein.

Veterinary Compositions

In accordance with the present disclosure, an intramammary veterinary composition is provided which comprises an agent which activates the OAS2 signalling pathway or induces expression of OAS2 in the mammary gland of a non-human mammalian subject and a pharmaceutically acceptable excipient or carrier, wherein the agent is present in an amount sufficient to reduce or shut down lactation in the non-human mammalian subject. Accordingly, the composition will be suitable for administration into the teat orifice or galactophore of a lactating non-human mammalian subject.

The pharmaceutically acceptable excipient or carrier is to be selected so as to be non-toxic, pharmaceutically acceptable, compatible with the active ingredients (i.e., the agent which activates the OAS2 signalling pathway or induces expression of OAS2), and of a viscosity to permit intramammary administration, whilst controlling the release characteristics of the agent.

In accordance with common practice, the veterinary composition according to the disclosure which is for intramammary administration comprises a suspension or solution of the active ingredient (i.e., the agent which activates the OAS2 signalling pathway or induces expression of OAS2) in a suitable carrier, which can be made of an aqueous or oily base. In one example, the carrier is saline. In another example, the carrier is an oily base. In another example, the carrier is saline.

Oils that can be used for the oily base in veterinary compositions are in general natural, e.g. vegetable, semi-synthetic or synthetic mono-, di- or tri glyceride. Vegetable oils that can be used are e.g., sesame oil, olive oil, cottonseed oil, castor oil, *arachis* oil, or coconut oil. The pharmaceutically acceptable carrier in the formulation according to the present disclosure may comprise an oily base and optionally one or more additives such as thickening agents, desiccants and antioxidants. Suitable pharmaceutical excipients are known in the art. Such pharmaceutical excipients for the carrier for intramammary formulations are e.g. described in "Gennaro, Remington: The Science and Practice of Pharmacy" (20th Edition, 2000), incorporated by reference herein.

Conventional thickening agents are e.g., aluminium stearate, silica, or fatty acid esters such as glycerol monostearate. A suitable amount of a thickening agent is within the range of 0 to 30% by weight.

Desiccants include e.g., silicates, activated clay, silica gel, and molecular sieve. Especially preferred is sodium aluminium silicate. A suitable amount of a desiccant that can be used is within the range of 0 to 15% by weight, preferably 0-10%.

Suitable antioxidants are e.g. butylhydroxytoluene or hydroxyanisole. The antioxidant will usually be present within the range of 0 to 10% by weight.

Other additives may also be present in the carrier in minor proportions.

The dosage volume of the intramammary veterinary composition may be varied according to subject to which the composition is to be administered. However, in a preferred example, the volume is sufficient to fill the mammary duct into which the composition is to be administered.

In one example, the veterinary formulation may further comprise an antimicrobial agent e.g., which is suitable for intramammary infusion, to prevent microbial infection in the mammary gland of a subject to whom the formulation is administered. In accordance with this example, the antimicrobial agent is included in the formulation as a preventative or prophylactic agent against microbial infection e.g., bacterial infection, in the mammary gland, whereas the agent which activates the OAS2 signalling pathway or induces expression of OAS2 is included in the formulation to reduce or shut down lactation in the non-human mammalian subject to whom the formulation is administered. As used herein, an "antimicrobial agent" is one which is bactericidal. Any antimicrobial agent which is suitable for administration by intramammary infusion is contemplated for use in the veterinary formulation of the present disclosure. Such antimicrobial agents are known in the art and contemplated herein.

In yet another example, the veterinary formulation may further comprise a further agent which shuts down or reduces lactation i.e., in addition to the agent which activates the OAS2 signalling pathway or induces expression of OAS2 in the mammary gland of a non-human mammalian subject. Any agent which shuts down or reduces lactation is contemplated for use in the veterinary formulation of the present disclosure. For example, the further agent which shuts down or reduces lactation may be an agent capable of increasing serotonin activity in a subject, for example, a serotonin-selective reuptake inhibitor (SSRI) as described in US Patent Publication No. 20150196507 (the content of which is incorporated herein by reference in its entirety). Other agents will be known to a person skilled in the art and are contemplated for use herein.

Methods of Administration

As described herein, the present disclosure provides a method of reducing or shutting down lactation in a non-human mammalian subject, comprising administering to the mammary gland of the subject an agent which activates the OAS2 signalling pathway or induces expression of OAS2 in the mammary gland of the subject. Suitable agents which activate the OAS2 signalling pathway or induce expression of OAS2 in the mammary gland of the subject are described herein and shall be taken to apply mutatis mutandis to any other example of the disclosure unless specifically stated otherwise.

The agent which activates the OAS2 signalling pathway or induces expression of OAS2 may administered in the form of an intramammary veterinary composition as described herein. Accordingly, the agent may be administered to the mammary gland of the non-human mammalian subject by intramammary or intraductal infusion.

The agent which activates the OAS2 signalling pathway or induces expression of OAS2 in the mammary gland will be administered to the non-human mammalian subject in an amount sufficient to reduce or shut down lactation in the subject. The actual dose of the agent which is sufficient to reduce or shut down lactation in a non-human mammalian subject will depend on the choice of agent used to activate the OAS2 signalling pathway or induces expression of OAS2 in the subject, the non-human mammalian animal to which the agent is being administered being treated, and/or the phase of lactation (i.e., early, mid and late lactation). The determination of those factors is well within the skill of a person skilled in the art. In accordance with an example of the method in which the agent to be administered to the non-human mammalian subject is poly (I:C), the agent is administered at a dose in the range of about 0.1 g/kg to about 15 μg/kg. In one example, the method comprises administering poly (I:C) to the non-human mammalian subject by intramammary or intraductal infusion at a dose of about 1 g/kg to about 10 μg/kg. In one example, the method comprises administering poly (I:C) to the non-human mammalian subject by intramammary or intraductal infusion at a dose of about 1.5 μg/kg to about 8.5 μg/kg. In one example, the method comprises administering poly (I:C) to the non-human mammalian subject by intramammary or intraductal infusion at a dose of about 1.5 μg/kg. In one example, the method comprises administering poly (I:C) to the non-human mammalian subject by intramammary or intraductal infusion at a dose of about 3.0 μg/kg. In one example, the method comprises administering poly (I:C) to the non-human mammalian subject by intramammary or intraductal infusion at a dose of about 5.0 μg/kg. In one example, the method comprises administering poly (I:C) to the non-human mammalian subject by intramammary or intraductal infusion at a dose of about 7.0 μg/kg. In one example, the method comprises administering poly (I:C) to the non-human mammalian subject by intramammary or intraductal infusion at a dose of about 8.5 μg/kg.

In one particular example, the method comprises administering poly (I:C) to the non-human mammalian subject by intramammary or intraductal infusion at a dose of about 1 mg to about 50 mg. In another example, the Poly (I:C) may be administered to the non-human mammalian subject by intramammary or intraductal infusion at a dose of about 1 mg to about 10 mg. For example, the Poly (I:C) may be adminstered to the non-human mammalian subject by intramammary or intraductal infusion at a dose of about 1 mg. For example, the Poly (I:C) may be adminstered to the non-human mammalian subject by intramammary or intraductal infusion at a dose of about 2 mg. For example, the Poly (I:C) may be adminstered to the non-human mammalian subject by intramammary or intraductal infusion at a dose of about 3 mg. For example, the Poly (I:C) may be adminstered to the non-human mammalian subject by intramammary or intraductal infusion at a dose of about 4 mg. For example, the Poly (I:C) may be adminstered to the non-human mammalian subject by intramammary or intraductal infusion at a dose of about 5 mg. For example, the Poly (I:C) may be adminstered to the non-human mammalian subject by intramammary or intraductal infusion at a dose of about 6 mg. For example, the Poly (I:C) may be adminstered to the non-human mammalian subject by intramammary or intraductal infusion at a dose of about 7 mg. For example, the Poly (I:C) may be adminstered to the non-human mammalian subject by intramammary or intraductal infusion at a dose of about 8 mg. For example, the Poly (I:C) may be adminstered to the non-human mammalian subject by intramammary or intraductal infusion at a dose of about 9 mg. For example, the Poly (I:C) may be adminstered to the non-human mammalian subject by intramammary or intraductal infusion at a dose of about 10 mg. However dosages in excess of 10 mg may be employed and are contemplated herein.

In one example, the method comprises administering the agent which activates the OAS2 signalling pathway or induces expression of OAS2 in a single dose to thereby reduce or shut down lactation in the non-human mammalian subject. In accordance with this example, the single dose will contain a sufficient quantity of the agent to reduce or shut down lactation in the subject. Preferably, the single dose will have a volume sufficient to fill the mammary duct into which the composition is to be administered.

Alternatively, or in addition, the method comprises administering repeat doses of the agent which activates the OAS2 signalling pathway or induces expression of OAS2 until lactation is reduced or shut down in the non-human mammalian subject. In one example, the method may comprise administering the agent to the non-human mammalian subject on a daily basis until lactation is reduced or shut down. In one example, the method may comprise administering the agent to the non-human mammalian subject every second day until lactation is reduced or shut down. In one example, the method may comprise administering the agent to the non-human mammalian subject every three days until lactation is reduced or shut down. In one example, the method may comprise administering the agent to the non-human mammalian subject once a week until lactation is reduced or shut down.

In each of the foregoing examples, reducing or shutting down lactation by performing a method as described herein may prevent mastitis in a non-human mammalian subject which is lactating. Preferably, the subject administered the agent which activates the OAS2 signalling pathway or induces expression of OAS2, or the intramammary veterinary composition comprising same, is not suffering from mastitis.

In one example, the method of the disclosure is capable of preventing mastitis in the absence of an antimicrobial agent being administered to the non-human mammalian subject. As used herein, an "antimicrobial agent" is one which is bactericidal. In one example, the method of the disclosure is performed in the absence of an antimicrobial agent being administered to the non-human mammalian subject. In accordance with this example, the method of the disclosure may consist essentially of administering to the mammary gland of the non-human mammalian subject by intramammary or intraductal infusion an agent which activates the OAS2 signalling pathway or induces expression of OAS2 in the mammary gland of the subject.

In an alternative example, the method of the disclosure further comprises administering to the non-human mammalian subject an antimicrobial agent e.g., by intramammary infusion, to prevent microbial infection in the mammary gland of the subject. In accordance with this example, the antimicrobial agent is administered as a preventative or prophylactic agent against microbial infection e.g., bacterial infection, in the mammary gland, whereas the agent which activates the OAS2 signalling pathway or induces expression of OAS2 is administered for the purpose of reducing or shutting down lactation in the non-human mammalian subject. In one example, the antimicrobial agent and the agent which activates the OAS2 signalling pathway or induces expression of OAS2 in the mammary gland may be administered separately e.g., sequentially. In another example, the antimicrobial agent may be administered together with the agent which activates the OAS2 signalling pathway or induces expression of OAS2 in the mammary gland e.g., in the same veterinary formulation. Any antimicrobial agent which is suitable for administration by intramammary infusion is contemplated for use in the method or veterinary formulation of the present disclosure. Such antimicrobial agents are known in the art and contemplated herein.

In yet another example, the method of the disclosure further may comprise administering to the non-human mammalian subject a further agent which shuts down or reduces lactation. In one example, the further agent which shuts down or reduces lactation and the agent which activates the OAS2 signalling pathway or induces expression of OAS2 in the mammary gland may be administered separately e.g., sequentially. In another example, the further agent which shuts down or reduces lactation may be administered together with the agent which activates the OAS2 signalling pathway or induces expression of OAS2 in the mammary gland e.g., in the same formulation. Any agent which shuts down or reduces lactation is contemplated for use in the method or veterinary formulation of the present disclosure. For example, the further agent which shuts down or reduces lactation may be an agent capable of increasing serotonin activity in a subject, for example, a serotonin-selective reuptake inhibitor (SSRI) as described in US Patent Publication No. 20150196507 (the content of which is incorporated herein by reference in its entirety). Other agents will be known to a person skilled in the art and are contemplated for use herein.

The agent which activates the OAS2 signalling pathway or induces expression of OAS2, and the intramammary veterinary composition comprising same as described herein, may be administered to a lactating subject from any non-human mammalian species in need to 'drying-off' or in whom lactation needs to be reduced e.g., such as to prevent mastitis, reduce fatigue and/or to wean young. In one example, the non-human mammalian subject for which the method, intramammary veterinary composition and/or kit of the disclosure is useful is a livestock species selected from the group consisting of cattle, buffalo, yaks, camelids, sheep, goats, pigs, horses, deer and donkeys. In one example, the livestock species is a ruminant species used for milk production for human consumption selected from the group consisting of cattle, buffalo, yaks, camelids, sheep and goats. In another example, the non-human mammalian subject for which the method, intramammary veterinary composition and/or kit of the disclosure is useful is a companion animal species selected from the group consisting of a cat, a dog, a horse, a rodent and a rabbit. In another example, the non-human mammalian subject for which the method, intramammary veterinary composition and/or kit of the disclosure is useful is a working animal selected from the group consisting of a horse, a dog, a mule, a donkey, a camel, oxen and a pig. In yet another example, the non-human mammalian subject for which the method, intramammary veterinary composition and/or kit of the disclosure is useful is a sporting animal selected from a horse and a dog.

Kits

The present disclosure also provides the agent which activates the OAS2 signalling pathway or induces expression of OAS2, or an intramammary veterinary composition comprising same, in a kit form. The kit may comprise a container. The kit typically contains the agent which activates the OAS2 signalling pathway or induces expression of OAS2, or the intramammary veterinary composition comprising same as described herein, with instructions for its administration e.g., by intramammary infusion. In some examples, the kit contains multiple doses of the agent or intramammary veterinary composition comprising same. In some example, the kit comprises the agent which activates the OAS2 signalling pathway or induces expression of OAS2, or the intramammary veterinary composition comprising same as described herein, packaged within an infusion canula for delivery. For example, each dose may be contained with a separate infusion canula.

In one example, the kit may comprise an antimicrobial agent. In one example, the antimicrobial agent is packaged separately to the agent which activates the OAS2 signalling pathway or induces expression of OAS2 or composition comprising same e.g., in a separate container. In another example, the antimicrobial agent and the agent which activates the OAS2 signalling pathway or induces expression of OAS2 are packaged together e.g., in the same container.

In one example, the kit may comprise a further agent which shuts down or reduces lactation. In one example, the further agent which shuts down or reduces lactation is packaged separately to the agent which activates the OAS2 signalling pathway or induces expression of OAS2 or composition comprising same e.g., in a separate container. In another example, the further agent which shuts down or reduces lactation and the agent which activates the OAS2 signalling pathway or induces expression of OAS2 are packaged together e.g., in the same container.

EXAMPLES

Example 1. Producing a Mutant Mouse Line for Failed Lactation

1. Production of an OAS2 Mutant Mouse Line

Using N-ethyl-N-nitrosourea (ENU) mutagenesis and a screen for failed lactation, a mouse line was established in which heterozygous (wt/mt) dams showed partial penetrance of poor lactation, producing litters that failed to thrive (FIG. 1), and homozygous (mt/mt) dams experienced complete failure of lactation (FIG. 1), providing a dominant pattern of inheritance.

1.1 Mice

All mice were housed in specific pathogen-free conditions at the Australian Phenomics Facility and the Garvan Institute, with all animal procedures approved by either the Australian National University or Garvan/St Vincent's Animal Ethics and Experimentation Committees. All animals were housed with food and water ad libitum with a 12-h day/night cycle at 22° C. and 80% relative humidity.

ENU mutagenesis and pedigree construction was carried out as previously described (Lo et al., 2012).

For quantification of lactation failure, litters were standardized to 7 pups per dam. Pups were weighed, as a group, at the same time daily. Mice were injected with BrdU dissolved in $H_2O$ (100 μg BrdU per gram body weight) 2 h prior to sacrifice by $CO_2$ asphyxiation, and mammary glands were collected. Mammary glands were either wholemounted and stained with Carmine alum or snap frozen in liquid nitrogen for mRNA and protein analyses.

1.2 Mapping and Sequencing

A pool of 15 affected F1 mice and a pool of 15 unaffected F1 mice were screened with a set of ~130 polymorphic markers between C57Bl/6 and CBA/CaJ mice that span the genome at 10-20 Mb intervals. Allele specific SNP primers were designed from a set of validated SNPs available on the world wide web at well.ox.ac.uk/mouse/INBREDS/. SNP genotyping was performed using the Amplifluor® kit (Chemicon) as per the manufacturers instructions. The confirmation and fine mapping were performed using Amplifluor® markers designed to amplify B6×CBA/CaJ SNPs within the linkage interval in individual affected and unaffected mice. Markers were designed at approximately 1-2 Mb distances within the initial map interval. More than 250 mice were screened from many successive cohorts of mice from backcrosses to CBA/CaJ to narrow the region to a 3 Mb interval. Sequencing of candidate genes was performed to locate the causal ENU base substitution using an affected mouse homozygous for the linkage region. Primers were designed for candidate genes to amplify all exons+/−15 bp to cover splice junctions. Sanger sequencing was used to identify the causal mutation by comparing the sequence of the affected individual against a C57Bl/6 mouse reference genome. Mutations were confirmed in a second affected individual and a C57Bl/6 wild type mouse.

1.3 Nimblegen Sequence Capture

The mapping was performed with the gsMapper program, which is part of the 454 software suite. The two samples (defined by Jersey_F4IC140 and Jerseypool) were mapped against the full region of the mouse genome on chromosome 5. The sequence used as reference is from genbank build37/UCSC mm9. Further analysis then focused on the reads mapped onto the target region: 118710087-123738720 on chromosome5.

Variation analysis detected where at least 2 reads differ either from the reference sequence or from other reads aligned at a specific location. SNPs, insertion-deletion pairs, multi-homopolymer insertion or deletion regions, and single-base overcalls and under calls are reported. Also, in order for a difference to be identified and reported, there must have been at least two non-duplicate reads that (1) show the difference, (2) have at least 5 bases on both sides of the difference, and (3) have few other isolated sequence differences in the read. Variations were classified as high-confidence if they fulfilled the following rules:

1. There must be at least 3 non-duplicate reads with the difference.
2. There must be both forward and reverse reads showing the difference, unless there are at least 5 reads with quality scores over 20 (or 30 if the difference involves a 5-mer or higher).
3. If the difference is a single-base overcall or under call, then the reads with the difference must form the consensus of the sequenced reads (i.e., at that location, the overall consensus must differ from the reference).

1.4 Genotype Analysis

Figure 2:
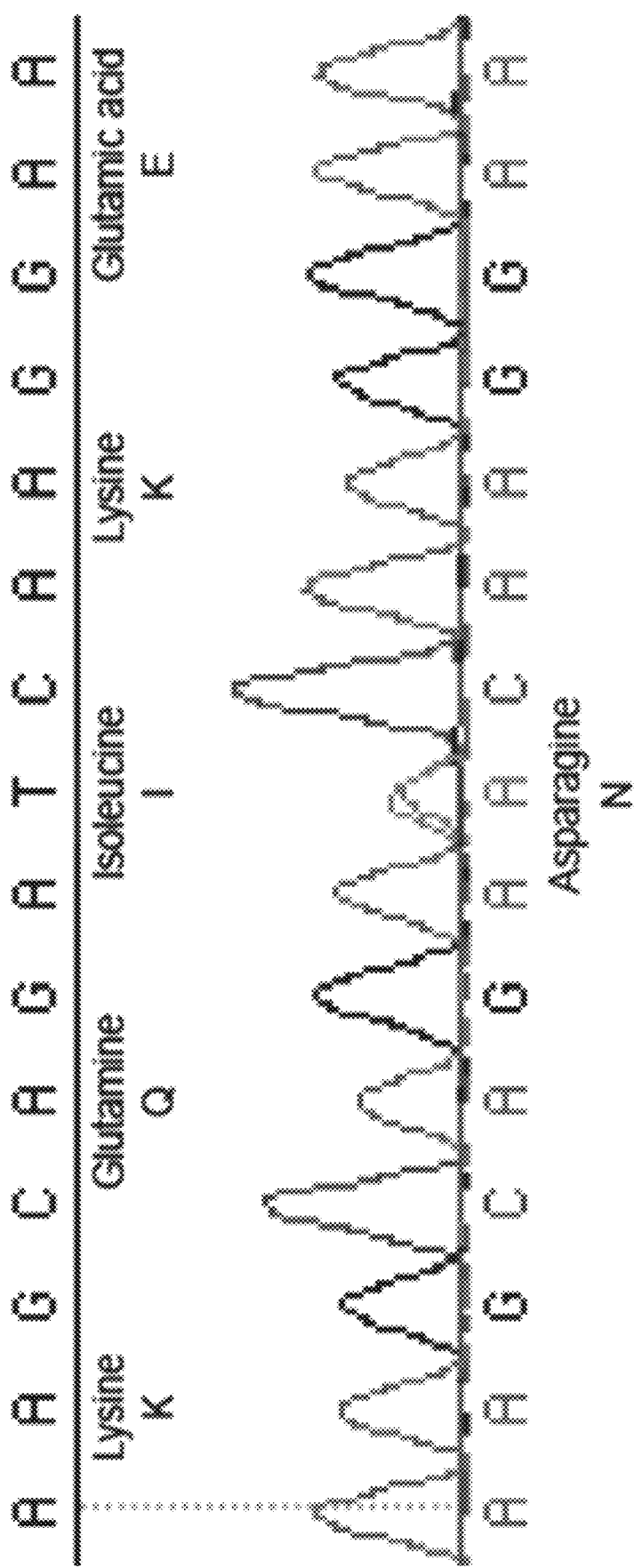
FIG. 2 illustrates the ENU-induced SNP mutation in OAS2 resulting in a change from isoleucine to asparagine.
Figure 3:
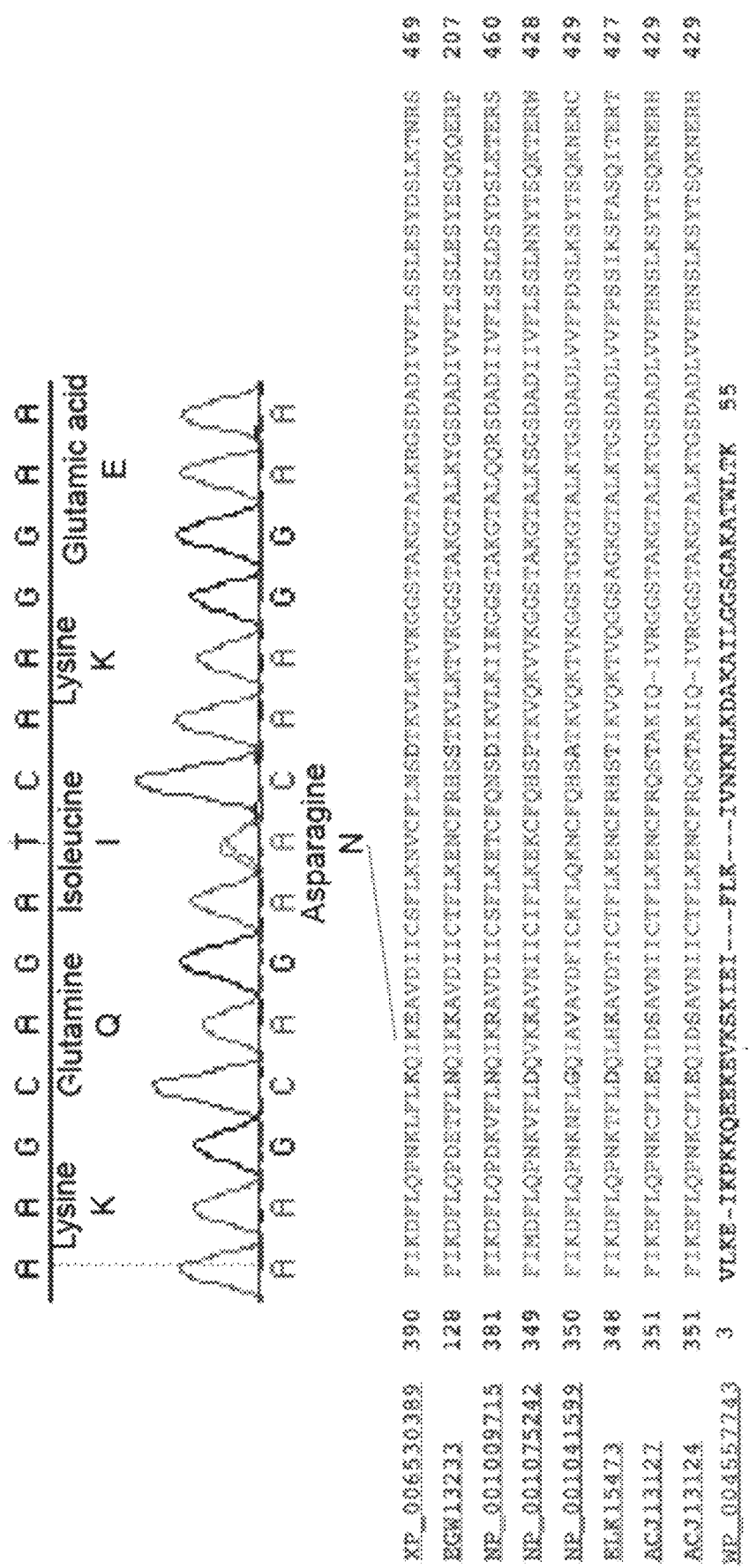
FIG. 3 illustrates (A) the SNP mutation in OAS2 resulting in an amino acid change, (B) conservation of the region containing the mutation in very diverse species including Archaea, and (C) the location of the mutation in relation to the active enzyme site of OAS2.
Figure 4:
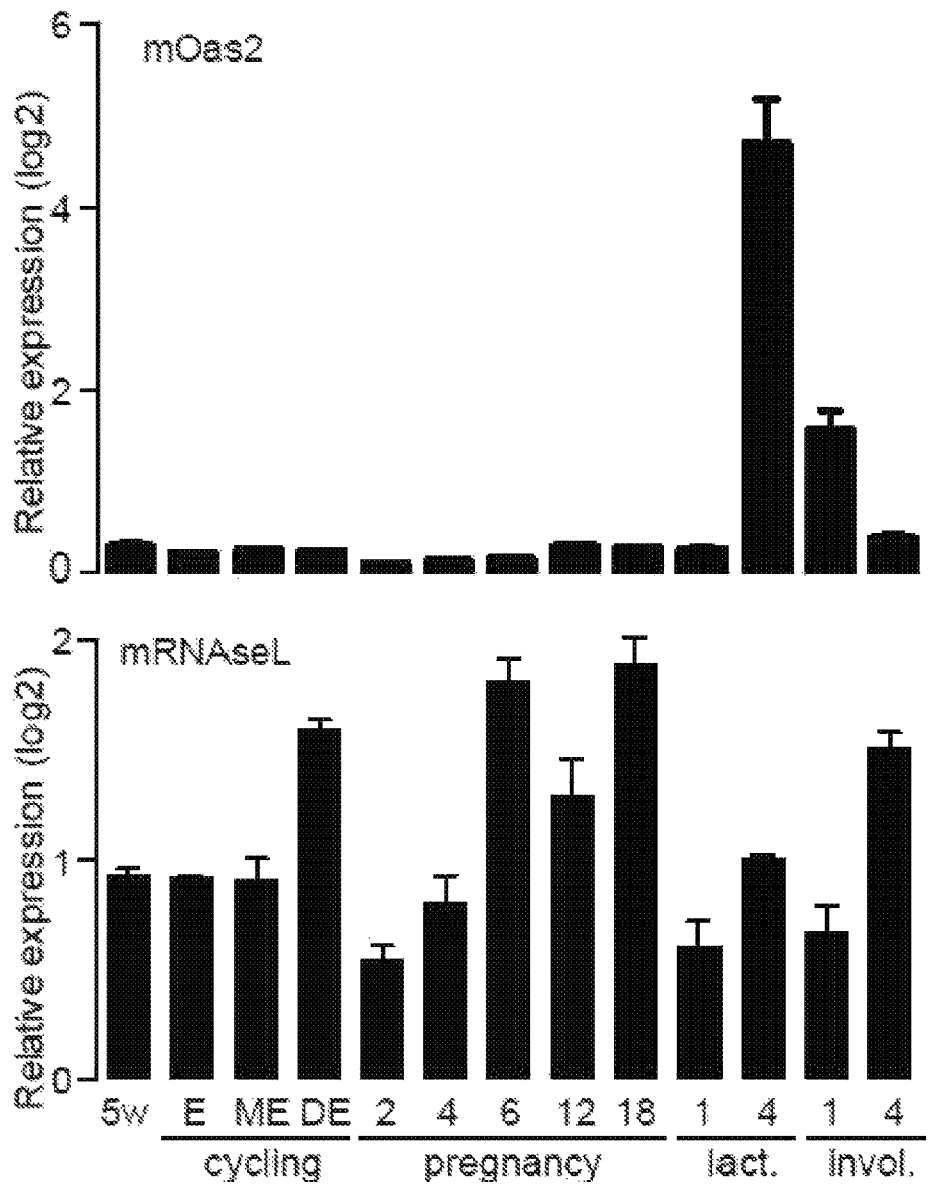
FIG. 4 illustrates the pattern of OAS2 and RNaseL expression in the mammary glands of wild type mice at various stages of mammary development as measured by quantitative PCR.
Figure 5:
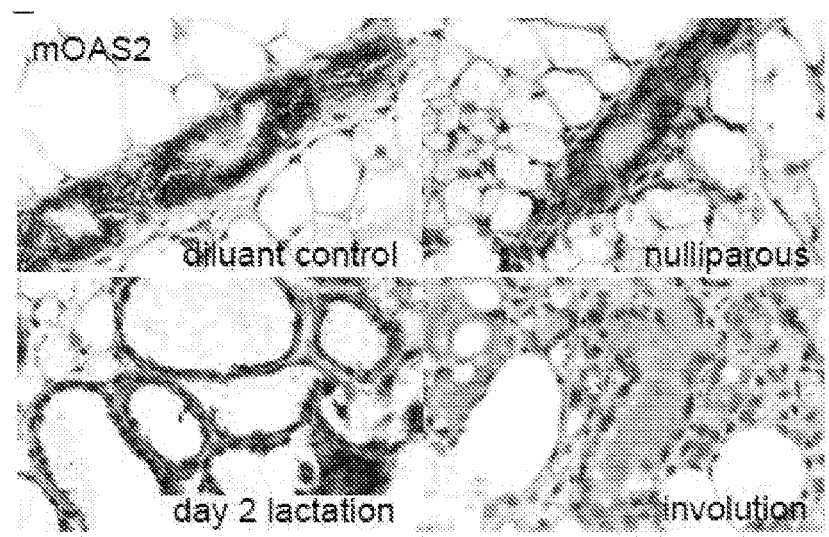
FIG. 5 provides immunohistochemistry for OAS2 in wild type mouse mammary glands.

PCR genotyping of polymorphic markers and their co-inheritance with lactation failure narrowed the mutation to a 4 Mb region of chromosome 5 between rs3662655 and rs2020515. Between 4-8 ENU mutations in 4 Mb was anticipated and the strategy proposed was to sequentially sequence exomes and then to experimentally validate when an exonic mutation was discovered. Sequencing revealed a T to A base change in OAS2, resulting in a non-conservative isoleucine to asparagine amino acid substitution (I405N; FIG. 2) in a conserved region of the OAS2 catalytic domain (FIG. 3). In wt/wt animals, OAS2 was expressed at a relatively low level until the establishment of lactation, when the level of OAS2 mRNA increased by 20 fold, and subsequently fell during early involution (FIG. 4). Using immunohistochemistry, corresponding changes in OAS2 levels in the mammary epithelium were also observed (FIG. 5).

The OAS2 mutation was discovered in a single G1 female and heritability of the phenotype confirmed by breeding with CBA CaJ male and cross fostering of pups.

1.5 OAS2 Mutant Mouse Line Maintenance and Genotyping.

After identification of the causative mutation, genotyping was performed using the following primers:

Forward-wildtype:
(SEQ ID NO: 1)
GCTCTTCCTAAAGCAGAT

Forward-mutant:
(SEQ ID NO: 2)
GCTCTTCCTAAAGCAGAA

Common reverse:
(SEQ ID NO: 3)
GGTGTCAGAATTCAAGAAGCAGAC

The OAS2 mutant colony was maintained by breeding heterozygous males (wt/mt) with wt/wt females. For the generation of homozygous experimental animals, wt/mt males were bred with wt/mt females and their offspring removed at 1dpp and fostered on a control mother.

A mouse line was thus established in which heterozygous (wt/mt) dams showed partial penetrance of poor lactation, producing litters that failed to thrive (FIG. 1), and homozygous (mt/mt) dams experienced complete failure of lactation (FIG. 1), providing a dominant pattern of inheritance.

Example 2. Characterisation of OAS2 Mutant Mouse Line 2.1 Methods 2.1.1 Histopathology and Organ Pathology A complete analysis of the histology and pathology of the Jersey strain was conducted by the Australian Phenomics Network (APN) Histopathology and Organ Pathology Service, University of Melbourne. Eight week and a 31 week female sibling pairs, comprised of mt/mt and wt/wt siblings, were examined macro and microscopically. Mammary tissue, ovaries, oviducts, bicornuate uterus, cervix, urinary bladder, liver/Gall bladder, cecum, colon, spleen/pancreas, mesenteric lymph node, stomach, duodenum, jejunum, ileum, kidney/adrenal, salivary glands/lymph nodes, thymus, lungs, heart, skin, eyes, brain, spinal cord, skeletal muscle, skeletal tissue/hind leg were macro and microscopically examined.

2.1.2 Expression of Milk Proteins in OAS2 Mutant Mouse Line

Quantitative PCR for mRNAs of milk proteins expressed in OAS2 mutant mouse line was performed. Briefly, total RNA was isolated from mammary tissue using Trizol reagent (mouse tissues; Gibco/Invitrogen Vic) or RNeasy® extraction kit (cell pellets; Qiagen) according to the manufacturer's instructions. Single stranded cDNA was produced by reverse transcription using 1 µg of RNA in a 20 µl reaction and diluted 1:5 with $H_2O$ (Promega). Quantitative PCR was performed using the Taqman probe-based system on the ABI 7900HT as per the manufacturer's instructions (Applied Biosystems).

TABLE 1

Taqman probes used for quantitative PCR.

| Gene | Probe (s) | Species |
|---|---|---|
| OAS2 | Mm00460961_m1 | Mouse |
| OAS2-2 | Mm01202789_m1 | Mouse |
| Wap | Mm00839913_m1 | Mouse |
| beta Casein | Mm0089664_m1 | Mouse |
| RNASEL | Hs00221692_m1 | Human |
| IRF7 | Hs01014809_g1 | Human |
| GapDH | Hs02758991_g1 | Human |
| GapDH | Mm99999915_g1 | Mouse |

2.1.3 Mammary Gland Whole Mounting and Immuno-Histochemistry

Mouse mammary glands were harvested from wt/wt and mt/mt mice and fixed in 4% buffered formalin for 4 hours. Glands were defatted in 3-4 changes of acetone before being dehydrated and stained in Carmine alum as previously described (Bradbury et al., 1995). Glands were then dehydrated in a series of graded alcohols and embedded in Paraffin for sectioning. Sections were either stained with haematoxylin and eosin for routine histochemistry or stained with antibodies to the following antigens using immunohistochemistry.

TABLE 2

Antibodies, concentration and antigen retrieval conditions for immunohistochemistry.

| Antigen | Antibody | Species reactivity | Retrieval | Primary antibody conc. | Secondary antibody |
|---|---|---|---|---|---|
| OAS2 | M18, sc49858 Santa-Cruz | Mouse/human | pH9 S2367 Pressure Cooker 15 secs | 1:200 | Goat Immpress-HRP (Vector Labs) MP7405 |
| Anti Milk | Accurate Chemical & Scientific CO. YNRMTM | mouse | pH6 Waterbath 20 mins | 1:12000 | Envision Rabbit (K4009) |
| Cleaved Caspase 3 | Asp175 5A Cell Signaling 9661 | Mouse/human | pH9 S2367 Pressure Cooker 30 secs | 1:100 | Envision Rabbit (K4009) |
| BrdU | Bu20a M0744 Dako | mouse | pH9 S2367 Waterbath 20 mins | 1:100 | Envision Mouse (K4007) |
| P-Stat1 | Tyr701 (58D6) Cell Signalling 9167 | mouse | pH9 S2367 Pressure Cooker 30 secs | 1:800 | Signal Stain Boost Cell Signalling 8114 |
| P-Stat5 | Tyr694 (C11C5) Cell Signalling 9359 | mouse | pH9 S2367 Pressure Cooker 30 secs | 1:600 | Signal Stain Boost Cell Signalling 8114 |

All reagents were from Dako unless otherwise specified. Visualisation was performed using the DAB+ liquid Substrate chromogen system (K3467).

2.1.4. Transcript Profiling wt/wt or mt/mt mice were time mated and mammary glands collected at day 18 of pregnancy or 2 days after partuition (2 dpp) and snap frozen in liquid $N_2$. Total RNA was isolated using Trizol reagent (Gibco/Invitrogen, Vic) and measured on the 2100 Bioanalyzer (Agilent). Total RNA from the mouse mammary glands was then labelled and hybridized to the Mouse Transcriptome Array (MTA) 1.0 as per the manufacturer's instructions (Affymetrix Ca, USA) at Ramiaciotti Centre for Genomics (UNSW, Sydney Australia). All mouse samples were prepared in biological triplicate for each experimental grouping. Microarray data are freely available from GEO: GSE69397 on the world wide web at ncbi.nlm.nih.gov/geo/query/acc.cgi?token=ohkleoespjotzoh&acc=GSE69397.

Quality control was performed using the Affymetrix Expression Console. Normalisation and probe-set summarization was performed using the robust multichip average method of the Affymetrix Power Tools apt-probeset-summarize software (version 1.16.1) (using the -a rma option). The transcript clusters with official HGNC symbols were then extracted from the HTA 2.0 arrays, resulting in 23532 gene transcript clusters. Differential expression between experimental groups was assessed using Limma (Smyth, 2004) via the limmaGP tool in GenePattern. Functionally associated gene-sets were identified using Gene Set Enrichment Analysis (GSEA) (Subramanian et al., 2005) on a ranked list of the limma moderated t-statistics, from each pair-wise comparison, against a combined set of 6947 gene-sets from v4.0 of the MSigDB (Liberzon et al., 2011) and custom gene-sets derived from the literature. Mouse gene-symbols were mapped to their human orthologs using the ensembl database. The Enrichment Map plugin (Merico, Isserlin, Stueker, Emili, & Bader, 2010) for Cytoscape (Shannon et al., 2003) was used to build and visualize the resulting regulatory network of gene-signatures, with conservative parameters: p=0.001; q=0.05; overlap s=0.5.

2.1.5 Cluster Generation Using Self-Organising Maps

The limma F-test statistic (Smyth, 2004), with a Benjamini-Hochberg adjusted p-value threshold of 0.05, was used to identify differentially expressed transcripts across the four experimental groups in the mouse expression arrays (wt/wt 2dpc, wt/wt 2dpp, mt/mt 2dpc, mt/mt 2dpp). This resulted in 660 significant transcript clusters.

Self-organising maps (SOMs), consisting of 6 nodes, were used to identify clusters of genes. The z-scores of the log 2 normalised gene-expression values, for each transcript cluster, were used as input to the biopython SOM algorithm implementation (Cock et al., 2009). The somcluster( ) parameters used were: iterations=50,000; nx=2, ny=3, init-tau=0.02, dist=Euclidean.

2.1.6 DAVID Functional Annotation Clustering

The db2db( ) function from the BioDBNet database (Mudunuri, Che, Yi, & Stephens, 2009) was used to convert gene-symbols to Ensembl gene IDs for input into DAVID (Jr et al., 2003). DAVID functional annotation clustering was carried out using the getTermClusterReport( ) function from the DAVID web services interface (Jiao et al., 2012), with the following parameters: overlap=3, initialSeed=3, finalSeed=3, linkage=0.5, kappa=50.

DAVID databases used: (BBID, GOTERM_CC_FAT, BIOCARTA, GOTERM_MF_FAT, SMART, COG_ONTOLOGY, SP_PIR_KEYWORDS, KEGG_PATHWAY, INTERPRO, UP_SEQ_FEATURE, OMIM_DISEASE, GOTERM_BP_FAT, PIR_SUPERFAMILY)

2.1.7 Functional Enrichment of Signature Gene-Sets

A Hypergeometric test was used to calculate the level of gene overlap between the genes identified in each SOM cluster and the MSigDB gene-set collections (Subramanian et al., 2005) and the custom functional signature gene-sets. A background set number, of 45956, as described on the MSigDB website, was used. A Benjamini-Hochberg (BH) corrected p-value was calculated for each set and a threshold of BH<0.05 was considered a significant enrichment. Mouse gene-symbols were mapped to their human orthologs using the ensembl database.

2.1.8 Polyacrylamide Gel Electrophoresis and Western Blotting

10 µg reduced protein was loaded in each well of 12% NuPAGE SDS polyacrylamide gels (Life Technologies) and separated using electrophoresis. Proteins were transferred to Immun Blot PVDF (Biorad) and Western blotted for mouse OAS2 (M-105, sc99098 Santa-Cruz), RNaseL (H-300, sc25798 Santa Cruz), E-cadherin (610182 BD Biosciences) and beta-ACTIN (AC-74, A5316, Santa Cruz).

2.2 Characterisation of OAS2 Mutant Mouse Line

2.2.1 Biology of the Mammary Glands

Figure 6:
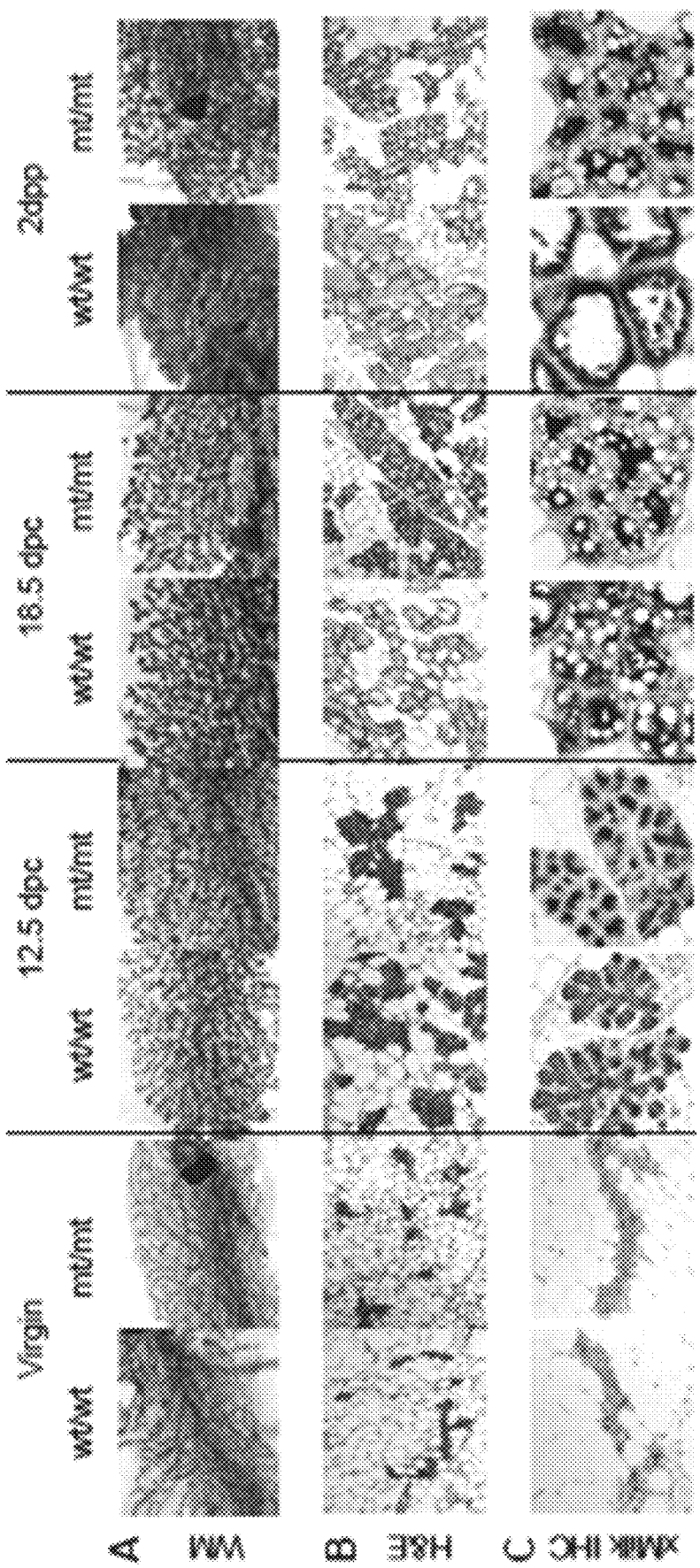
FIG. 6 illustrates the mammary phenotype at key stages of mammary development. (A) Whole mount histology of the 4th inguinal mammary gland showing ductal development in mature virgin mice (8-10 weeks old) and lobulo-alveolar development at 12.5 days post coitus (dpc), 18.5 dpc and 2 days post partum (2dpp) in wild type mice (wt/wt) or homozygous mutant mice (mt/mt). (B) Corresponding hematoxylin-eosin histochemistry. (C) Corresponding immunohistochemistry for milk protein expression using an antibody raised against whole mouse milk. (D) Corresponding western blot for milk proteins using the anti mouse milk antibody and keratin 18 loading control. Molecular size is shown together with the established sizes of the indicated milk proteins. Lactoferrin (LF), serum albumin (SA), caseins α, κ, β, γ and ε, whey acidic protein (wap) and alpha lactalbumin (aLac).
Figure 7:
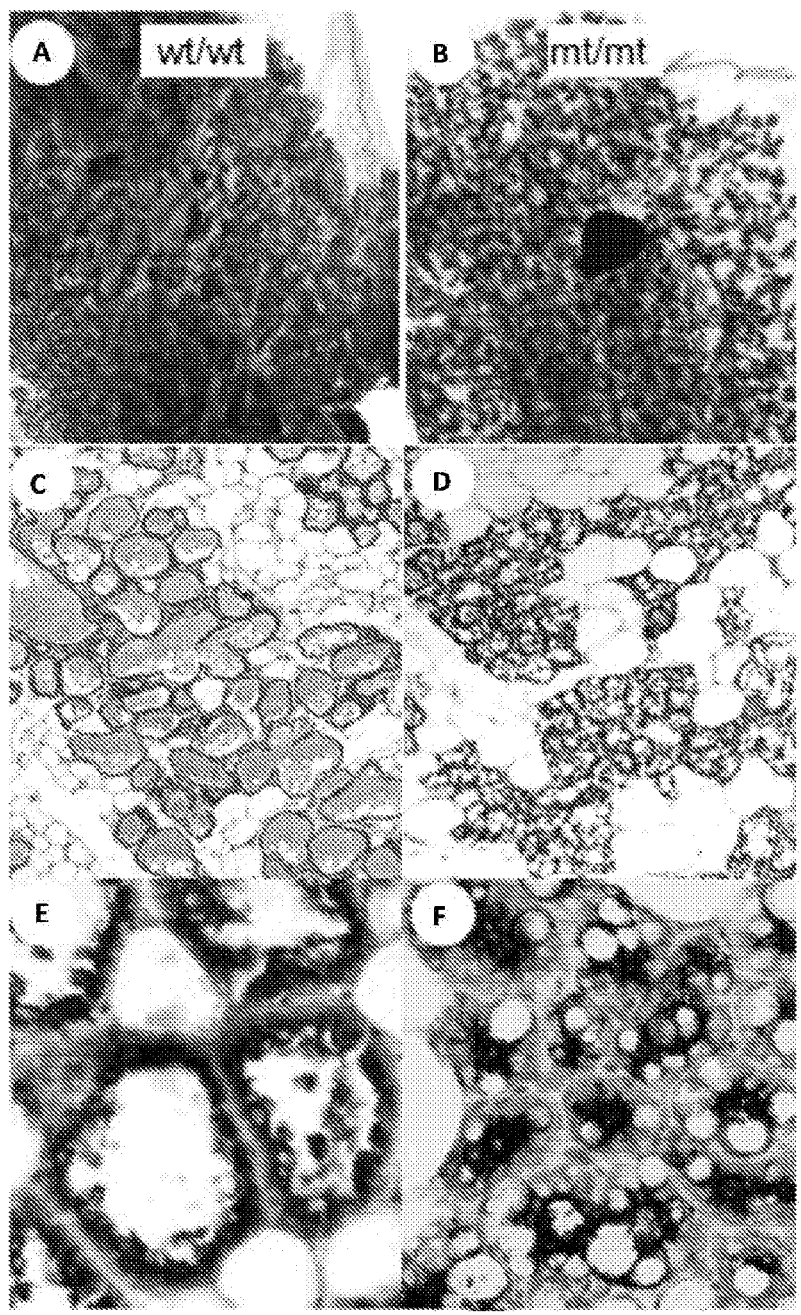
FIG. 7 provides: (A and B) whole mount histology of the 4th inguinal mammary gland showing lobuloalveolar development at 2 days post partum (dpp) in wt/wt or mt/mt mice, respectively; (C and D) corresponding haematoxylin-eosin histochemistry; and (E and F) corresponding immunohistochemistry for milk protein expression.
Figure 8:
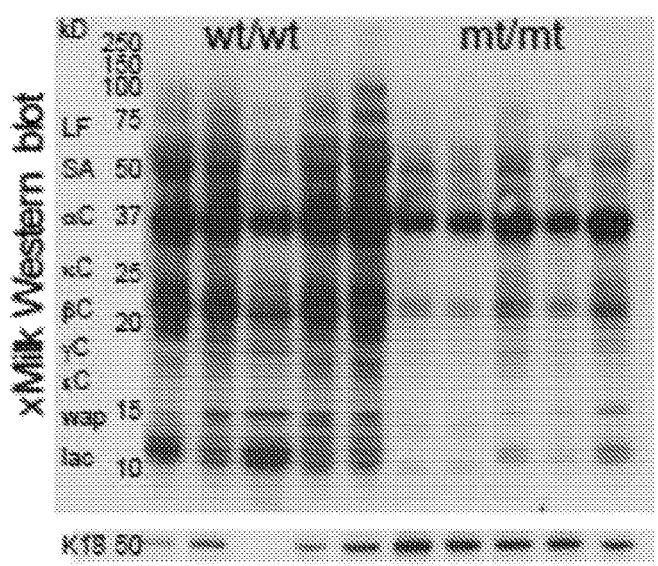
FIG. 8 is a western blot for milk proteins expressed in the mammary gland in wt/wt and mt/mt mice 2 days post partum (dpp). Molecular size is shown together with the established sizes of the indicated milk proteins. Lactoferrin (LF), serum albumin (SA), caseins α, κ, β, γ and ε, whey acidic protein (wap) and alpha lactalbumin (lac).

Development of the mammary ductal network during puberty, and of the lobulo-alveolar units during pregnancy, was normal in mt/mt dams (FIGS. 6A and B). The onset of milk protein synthesis also showed no defects during pregnancy by immunohistochemistry or western blot (FIGS. 6C and D). Lactation failure in mt/mt mice at 2 days postpartum (2dpp) was seen as smaller alveoli, failure of alveolar expansion and retention of lipid droplets and colostrum (FIG. 7A-F). Western blotting for milk (FIG. 8 and FIGS. 6C and D) showed greatly reduced expression of all the major milk components at 2dpp relative to the level of the epithelial cell marker cytokeratin 18.

2.2.2 Expression of Milk Proteins

Figure 9:
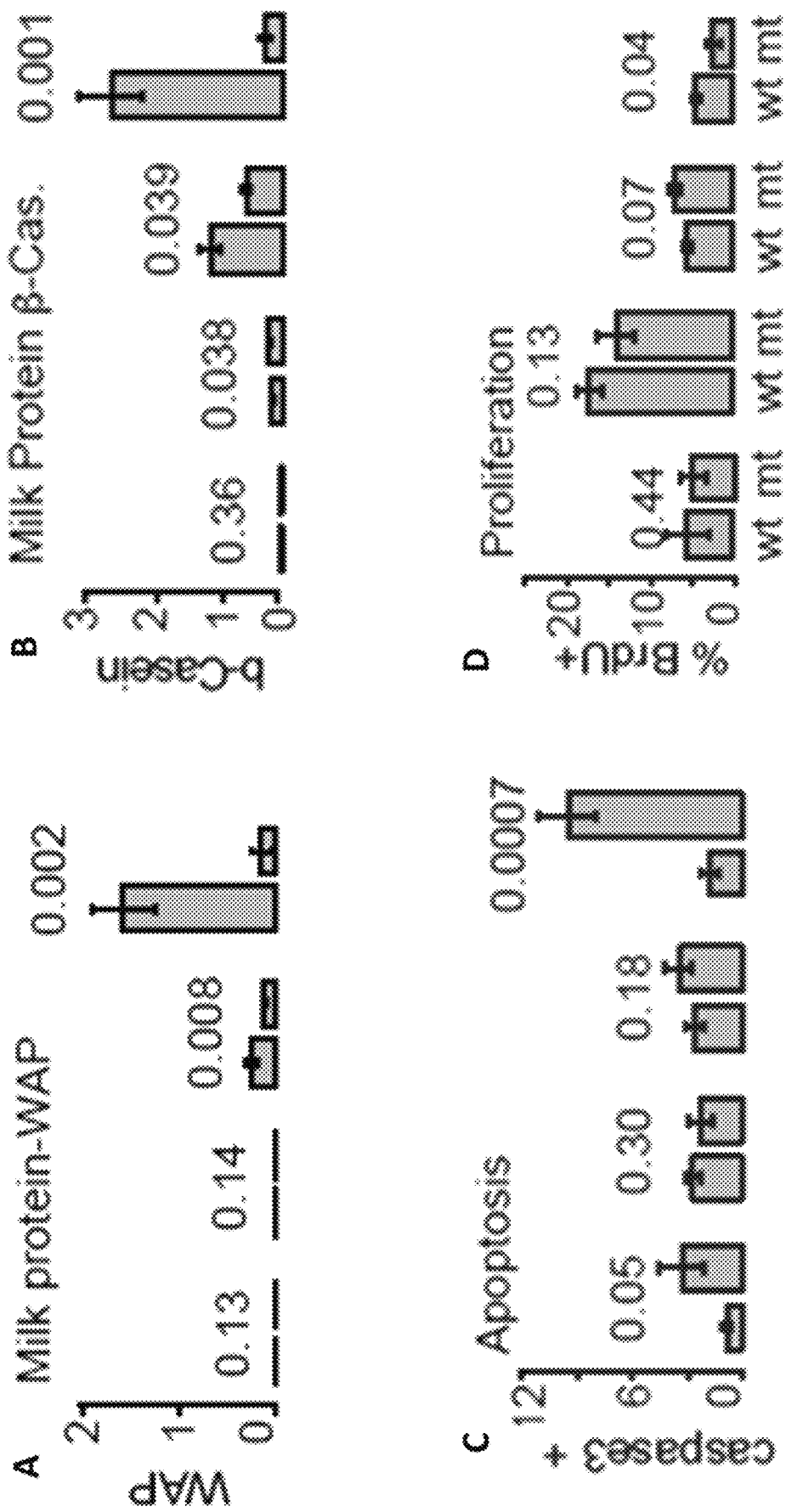
FIG. 9 presents the following (A) Quantification of Wap mRNA by qPCR at in wt/wt or mt/mt mice; (B) Quantification of β-casein (β-Cas) mRNA by qPCR; (C) Quantification of epithelial cell death by immunohistochemistry for cleaved caspase 3, results are the number of positively stained epithelial cells as a percentage as a percentage of total number of epithelial cells per field; (D) Quantification of epithelial cell proliferation by incorporated BrdU expressed as a percentage of total number of epithelial cells per field; (E and F) Immunohistochemistry for phosphorylated (P) Stat1 expression at 2 days post partum (dpp) in wt/wt or mt/mt mice; (G) Quantification of P-Stat1 expression in wt/wt or mt/mt mice by immunohistochemistry, results are the number of positively stained epithelial cells as a percentage of total epithelial area; (H) Quantification of P-Stat1 expression in wt/wt or mt/mt mammary transplants by immunohistochemistry, results are the number of positively stained epithelial cells as a percentage of total epithelial area; (A-B and G) wt/wt n=4-5 mice, mt/mt n=3-5 mice per time point (H) wt/wt n=3-5 mice, mt/mt n=2-5 per time point. Student's t-test p values are given, error bars are standard error of the mean.

Quantitative PCR for the mRNAs for the milk proteins whey acidic protein (WAP) β casein -Cas) showed reduced levels in mt/mt dams (mt) compared to wt/wt dams (wt) at 18 days post-coitus (dpc) and especially at 2dpp (FIGS. 9A and B). The number of cleaved-caspase 3 positive epithelial cells increased (FIG. 9C) and BrdU incorporation by the epithelium was reduced, indicating increased cell death rate and decreased cell proliferation respectively (FIG. 9D).

2.2.3 Stat1 Activation in OAS2 Mutant Mouse Line

Immunohistochemistry was used to examine Stat1 activation. In wt/wt dams at d18.5 of pregnancy and 2 days post partum, scattered regions of phosphorylated Stat1 staining in tightly packed areas of small and unexpanded alveoli was observed (FIG. 9E). These regions were very rare at the other stages of development examined. In mt/mt animals, Stat1 phosphorylation was again seen within regions of small unexpanded and tightly packed alveoli (FIG. 9F), but at day 18.5 of pregnancy, these regions of Stat1 phosphorylation occurred at a far greater frequency than in wt/wt glands, and instead of receding in the post partum period like wt/wt glands, the frequency of this pattern of staining increased further (FIG. 9G).

Stat1 phosphorylation was also examined in mammary glands formed by transplant of epithelium from mt/mt or wt/wt animals into the mammary fat pads of prepubescent wild type mice cleared of endogenous epithelium. A statistically significant increase in Stat1 phosphorylation was again observed in mt/mt transplants in the pre-partum period (transplants can't interrogate the post partum period), demonstrating that the ENU-mutation operates autonomously via the mammary epithelial cell (FIG. 9H).

2.2.4 RNA Transcript Profiling

Figure 10:
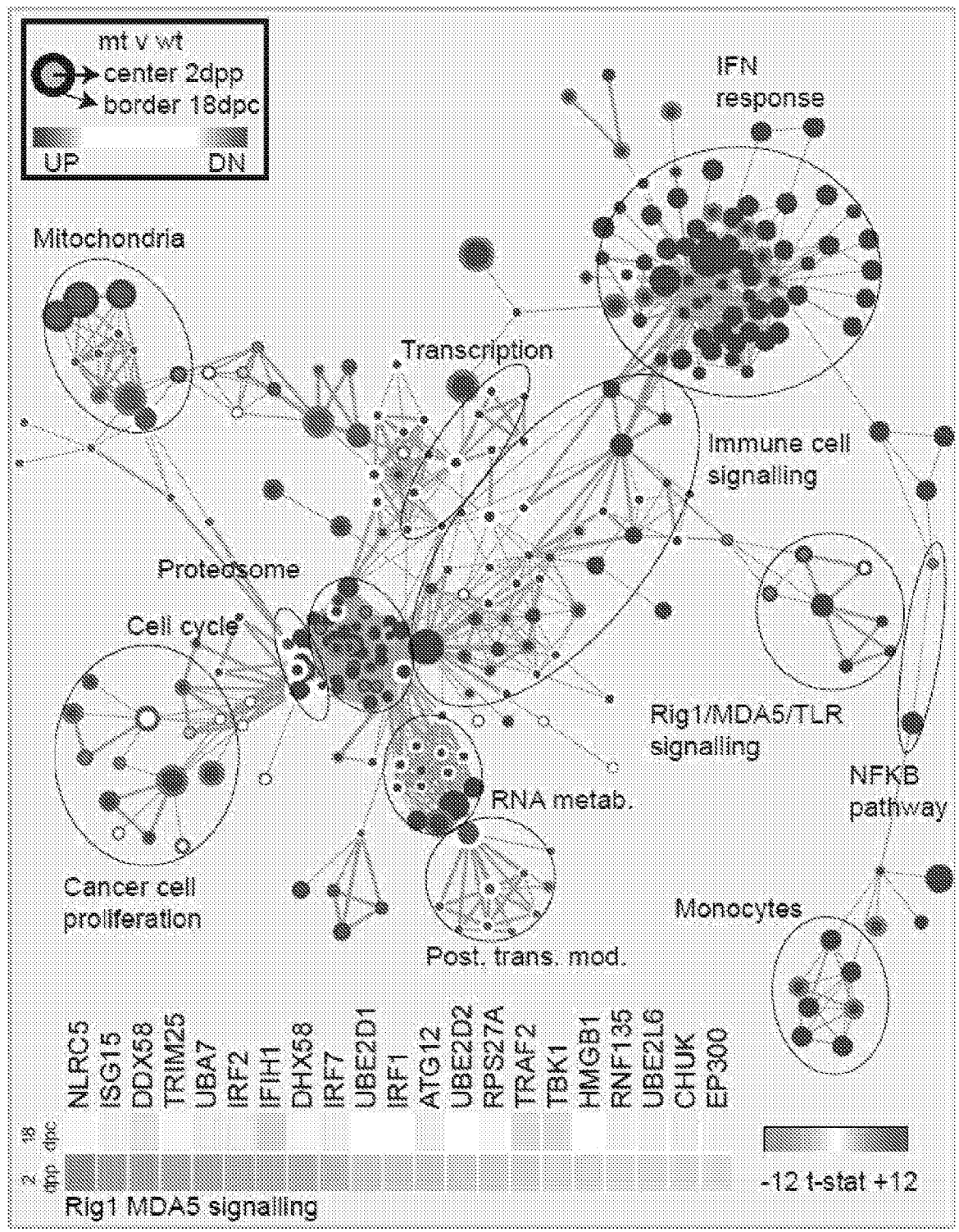
FIG. 10 illustrates the effects of OAS2 mutation on global patterns of gene expression in the mammary gland. Whole mouse mammary glands from homozygous OAS2 mutant (mt) or wild type (wt) animals were profiled using Affymetrix MTA arrays. Differential gene expression was ranked by the limma t-statistic and this was used as the input for gene set enrichment analysis to identify functional signatures. The enrichment-map plug in for Cytoscape was used to visualize the results. Each node represents a gene set and the expression of genes comprising the leading edge of some of these sets is shown as heat maps of the t-statistic. Labels indicate the function of the clustered gene sets. Gene expression in mt animals is compared with wt animals at 2dpp (node centre colour) or 18dpc (node edge colour).
Figure 11A:
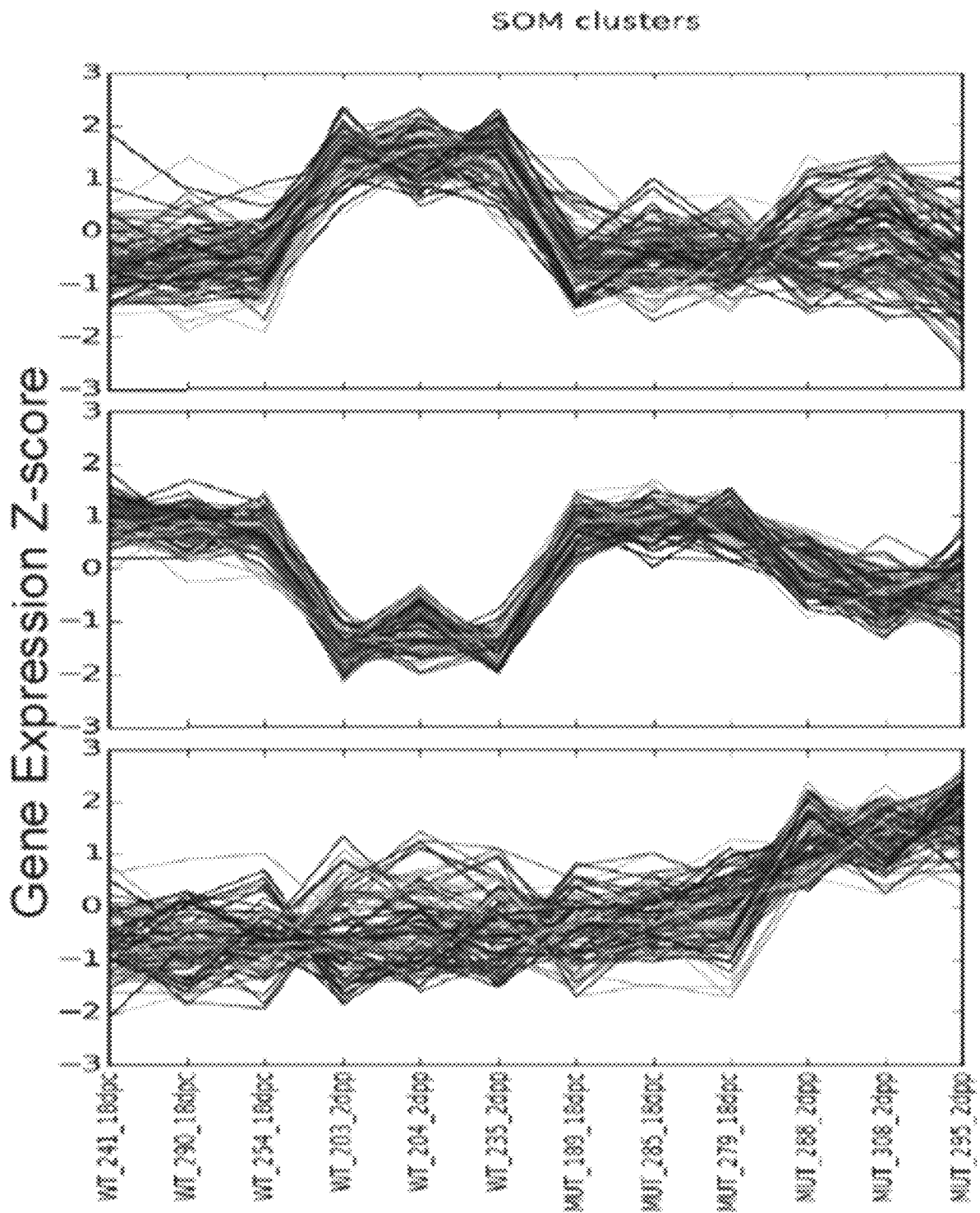
FIG. 11 provides self organizing maps to identify functional expression signatures: (A) Gene expression changes induced in mouse mammary gland by expression of mutant or wild-type OAS2, resolved into 6 patterns; and (B) Corresponding functional groups uniquely contained within each of the gene expression patterns from the top panel. The top-5 functions in each category (DAVID, MolSig DB Hallmark sets, Transcription factor sets (TFT), our set of Involution and lactation profiles and MolSig DB pathways sets) are shown as scored either by the DAVID enrichment score or the BH corrected p-value from the hypergeometric test.
Figure 11B:
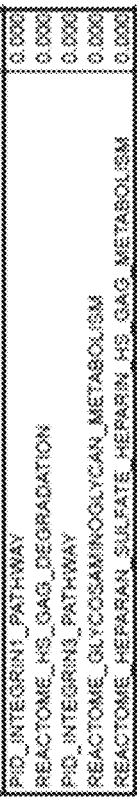

Affymetrix Mouse Transcriptome Assay (MTA) 1.0 GeneChip was used to measure changes in gene expression underlying these events. Profiling of RNA transcripts was performed in the mammary glands at 18dpc and 2dpp from wt/wt and mt/mt mice. A Gene Set Enrichment Analysis (GSEA) of genes was carried out using the Limma t-statistic as a measure of ranked differential expression and visualized with the Enrichment Map plugin for Cytoscape. Gene expression changes were compared between mt/mt and wt/wt mice at 18dpc or 2dpp (FIG. 10). This identified a robust enrichment of a prominent cluster of gene sets involved in the interferon response in postpartum mt/mt but not wt/wt mammary glands, which increased in magnitude between 18dpc and 2dpp. Genes in these sets included the interferon-induced genes Isg15, Mx1, Rsad2, Oas1, OAS2 and OasL. Interferon induced genes involved in the molecular pattern response pathway were also induced, such as Ddx58 (RIG-1), Dhx58 (RIG-1 regulator), Mavs and Nlrc5 (NODS). Additional downstream transcriptional regulators of the interferon response, such as Stat1, Irf7 and Irf9, were upregulated. In mt/mt glands this was accompanied by increased expression of a broad range of mitochondria-associated cell death genes such as Tnsfs10 (TRAIL), Acin1, Birc2, Traf2, Bcl2l1 (BCL-XL), Bcl2l11 (BIM), Apaf1, Dffb, Xaf and Ripk1. Very similar results were obtained using an independent analysis technique based on self-organising maps (FIGS. 11A and B). This transcriptional data indicates that a robust interferon response is induced by the mutation.

2.3 Discussion

These experiments show that the OAS2 mutation caused activation of OAS2 driven signalling to prevent the activation of lactation in the post partum period. The effect of the mutation could be detected via Stat1 activation from mid pregnancy and was only required in the mammary epithelial cell for effect.

Lactation failure and milk stasis characterize mastitis. The major consequence of mastitis is reduced weight-gain of the infant, precipitating a switch to bottle-feeding where available, or reduced neonatal health where it is not. The results presented herein suggest that the OAS2 pathway may be involved in its pathogenesis. The results presented herein also show that stimulation of the OAS2 pathway can produce a persistent interferon response that prevents activation of Stat5, which is essential for activation of milk secretion during the post partum period, and was only required in the mammary epithelial cell for effect. Thus, the results presented herein also support to use of OAS2 activators to prevent, reduce or shut down lactation, which may be useful as a preventative of mastitis.

Example 3. Intramammary Infusion of Poly (I:C) to Mice During Lactation

In this example, the inventors demonstrate that Poly (I:C) (a representative OAS2 activator) can reduce or shut down lactation when administered to lactating mice via intramammary infusion. The results show that the administration of Poly (I:C) resulted in lactation failure, precocious involution and mammary alveolar remodelling, such that the infused mammary glands in a previous pregnancy can recover and become fully lactation competent following a subsequent pregnancy.

3.1 Methods

Stock Poly (I:C) solution was diluted in sterile saline at a concentration of 10 mg/ml and then heated to 50° C. as per the manufacturer's instructions. From this stock solution, treatment and control solutions for injection to the mammary glands of mice were formulated as follows:

TABLE 3

Injection master mix for 25 ng/µl Poly (I:C)

| Ingredient | For 1 mouse | For 50 mice |
|---|---|---|
| 1:100 Poly (I:C) Sigma P1530 (10 mg/ml (10 µg/µl) stock diluted to concentration of 0.1 µg/µl (100 ng/µl) | 0.5 (50 ng) or 1 µl (100 ng) | 50 µl (final concentration 25 ng/µl) |
| Saline (Gibco PBS) #10010023 | 3.4 (for 50 ng) or 2.9 µl (for 100 ng) | 145 µl |
| 0.4% Trypan blue stock (ThermoFisher #15250061) | 0.1 µl (final conc. 0.01%) | 5 µl (final conc. 0.01%) |
| Total intraductal injection volume | 4 µl (for 100 µL, Poly (I:C)) 10 µl (for 250 ng Poly (I:C)) 20 µl (for 500 ng Poly (I:C)) | NA |

TABLE 4

Injection master mix for vehicle control

| Ingredient | For 1 mouse | For 20 mice |
|---|---|---|
| Saline (Gibco PBS) | 3.9 µl | 195 µl |
| 0.4% Trypan blue stock (ThermoFisher #15250061) | 0.10 µl (final conc. 0.01%) | 5 µl (final conc. 0.01%) |
| Total intraductal injection volume | 4 µl vehicle or 10 µl vehicle or 20 µl vehicle | NA |

Figure 12:
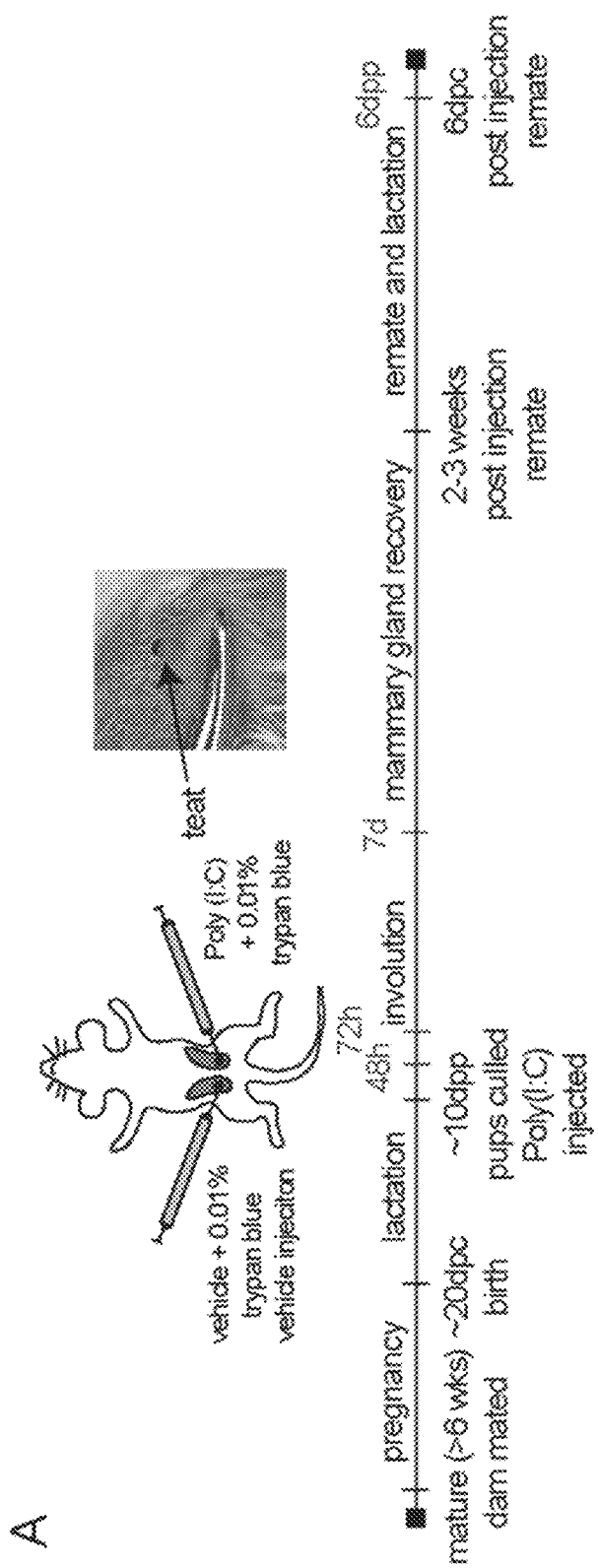
FIG. 12 is a schematic diagram illustrating the process of intramammary infusion by intraductal injection of Poly (I:C) during lactation to activate OAS2 signalling pathway and reduce or shutdown lactation. (A) Schematic diagram illustrating the experimental timeline for intraepithelial administration of Poly (I:C) to mice. (B) Photo pictorial illustration of intraepithelial administration of Poly (I:C) into the inguinal mammary glands of mice. dpc: days post coitus, dpp: days post partum, arrows: injection sites, arrowheads: teats.

Briefly, mice were mated, allowed to give birth and establish lactation for 6-10 days, at which time the pups were euthanized and Poly (I:C) or saline vehicle control was intraductally injected into the left and right $4^{th}$ (inguinal) mammary glands respectively via intramammary mammary infusion directly into the galactophore as shown in FIG. 12. The teats of the inguinal mammary glands of lactating mice (at 6-10dpp) were prepared by removing approximately 0.2 mm of the tip of the teat to open the galactophore and expose the main mammary sinus. A blunt ended 50 µl 30/12.7 mm/3 Hamilton syringe was then used to inject a single dose of the treatment or control solution (as appropriate) into the main sinus via the open galactophore. The treatment doses contained 50 ng, 150 ng, 250 ng or 500 ng Poly(I:C) in volumes of 4 µl, 4 µl, 10 µl and 20 µl sterile PBS containing 0.01% trypan blue respectively (prepared according to Tables 3 and 4). After injection, teats were either sealed with surgical wound glue (e.g., Histoacryl) or left to heal.

Figure 13:
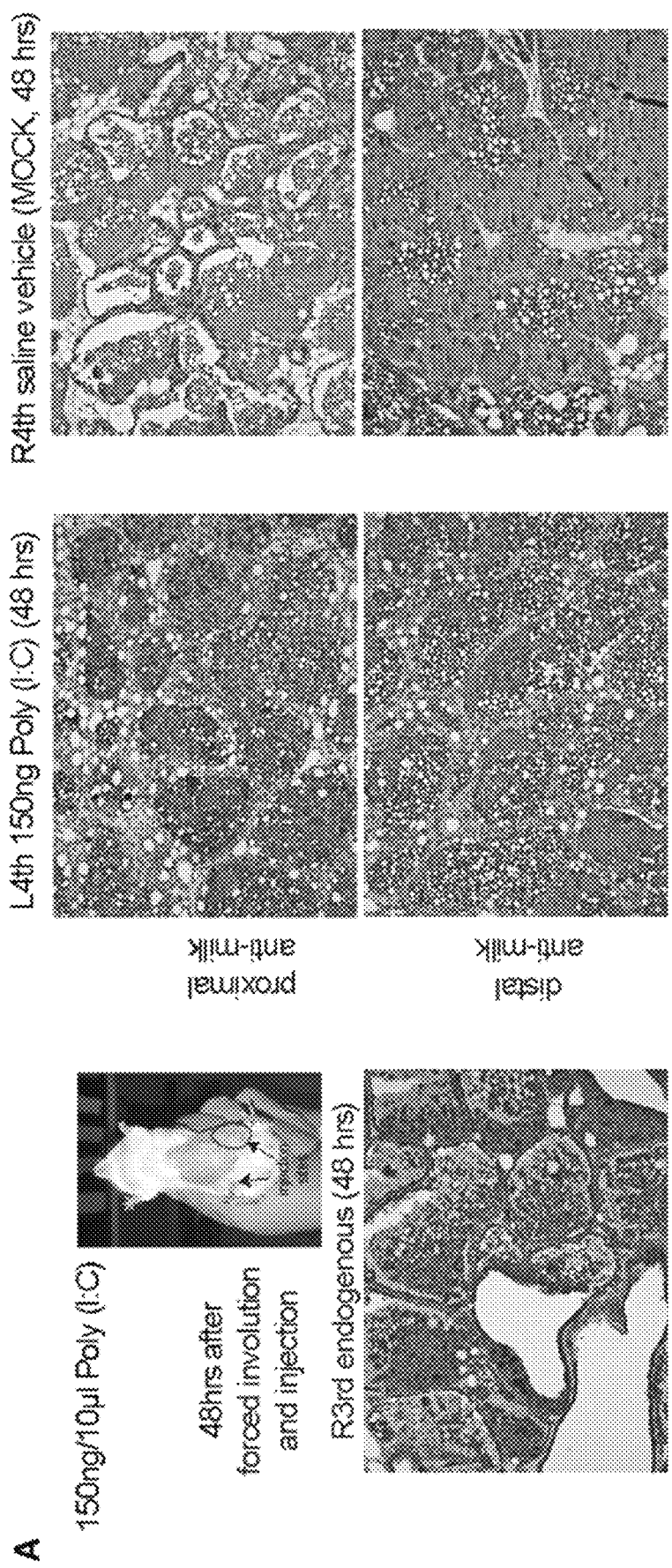
FIG. 13 illustrates that Poly (I:C) intramammary infusion results in neutrophil accumulation, alveolar collapse, lactation failure and precocious involution. Injection of Poly (I:C) was visualized by observing the proximal area underneath the skin surrounding the 4th teat, which when compared to distal region of the same mammary gland lacked the white milk engorged area (left hand side of panels A-C). The photomicrographs on the right hand side of the panels A-C depict DAB+ immunohistochemistry using a rabbit antibody raised against mouse Milk in the mammary glands proximal or distal the inguinal teat from mice injected with either Poly (I:C) (left (L) mammary gland) or vehicle control (right (R) mammary gland) and collected at either 48 hrs (top panels), 72 hrs (middle panels) or 7 days (lower panels) after injection and forced involution. The $3^{rd}$ (axial) endogenous mammary glands are used as a control.

At 24 hours, successful injection of Poly (I:C) was visualized by observing the proximal area surrounding the 4th teat underneath the skin, which when compared to distal region of the same mammary gland lacked the white milk engorged area. The injection area was also visualised using the trypan blue dye, which penetrated approximately 25% of the inguinal mammary gland area directly adjacent (proximal) to the teat (FIG. 13, black arrows). Forced involution was produced by removing pups at the time of injection.

At 48 hrs, 72 hrs or 7 days post-injection (i.e., 48, 72 and 7 days post involution), mice were euthanized and mammary glands collected, or alternatively they were left to recover for 2-3 weeks after injection, re-mated and euthanized following 6 days of lactation (6dpp) at which time the mammary glands were collected.

Analysis concentrated on the regions of the glands proximal to the infusion site, where the infusion had filled the mammary ducts, and a region distal to the infusion site which the infusion did not reach.

To assess lactation in the mammary gland, immunohistochemistry was performed on mammary glands collected at 48 hours, 72 hours and 7 days following injection with Poly (I:C) or saline vehicle control according to the methods described in Example 2 and using a rabbit antibody against mouse milk (Accurate Chemical & Scientific Corporation, as described in Table 2).

As increased phosphorylated Stat1 and a corresponding decrease in phosphorylated Stat5 was observed in the OAS2 mutant mice at lactation (Example 2), immunohistochemistry was performed according to the methods described in Example 2 using antibodies to pStat1, pStat5 and Milk (Table 2) on mammary glands infused with 150 ng (5 g/kg) (Poly (I:C), saline control alone or endogenous R3rd mammary glands to determine the effect of poly (I:C) infusion on Stat1 and Stat5.

3.2 Results:

3.2.1 Poly (I:C) Intramammary Infusion Results in Neutrophil Accumulation, Alveolar Collapse, Cessation of Lactation and Precocious Involution.

At 24-48 hours after injection and pup removal, milk engorgement was observed as white areas directly underneath the dermis over inguinal ($4^{th}$) and axial ($3^{rd}$) mammary gland regions, which were starkly silhouetted by the dark colour of the peritoneum of shaved mice. The regions proximal to the main mammary sinus infused with Poly (I:C) did not appear engorged with milk (darker areas, red dotted lines, FIG. 13) when compared to distal regions of the same gland, or to the proximal regions of mammary glands infused with saline-vehicle alone.

Immunohistochemistry using the antibody raised against mouse milk confirmed the loss of milk in the proximal regions of the left Poly (I:C) infused glands at 48 hours (FIG. 13, top panels) and 72 hours (FIG. 13, middle panels) after infusion. The right saline-infused glands of the same mouse had distended alveoli filled with milk (dark staining). Neutrophil accumulation in the alveoli and the extracellular tissues was also observed in the proximal regions of the Poly (I:C) infused glands, which was also evident to a lesser extent in the distal regions of the same gland, showing that an inflammatory response had spread from the injected site. Alveolar collapse was also observed in the proximal regions of Poly (I:C) treated glands and early time points, and by 7 days post Poly (I:C) infusion this had progressed to extensive tissue remodelling in the Poly (I:C) injected glands (FIG. 13, L4th lower panels) when compared to the saline control glands. For all mice, a control non-injected (R3rd endogenous gland) was used as an additional non injected control.

Figure 14:
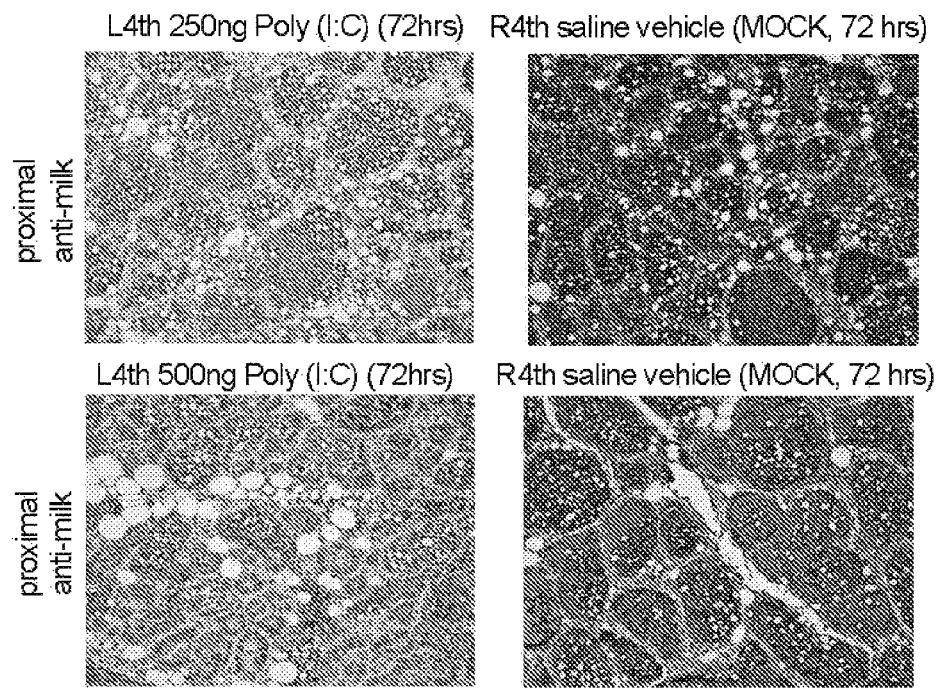
FIG. 14 illustrates that Poly (I:C) intramammary infusion results in neutrophil accumulation, alveolar collapse, lactation failure and precocious involution. The photomicrographs depict DAB+ immunohistochemistry using a rabbit antibody raised against mouse Milk in the region proximal the inguinal teat of mammary glands from mice injected with either a single dose of 250 ng or 500 ng Poly(I:C) in volumes of 10 and 20 µl sterile PBS respectively (left (L) mammary gland) and vehicle control (right (R) mammary gland), collected at 72 hrs after injection and forced involution.

Higher concentrations of Poly (I:C) 250-500 ng/injection (8.3-16.7 µg/kg) resulted in more severe defects in alveolar integrity and milk accumulation 72 hours after injection, with the highest dose of 500 ng (16.7 µg/kg) injection producing the most profound effect (FIG. 14), demonstrating a dose-dependent effect. Neutrophil accumulation in the glands was evident, alveoli had reduced in size or collapsed and the accumulation of milk was reduced. The proximal regions of the L4th mammary glands infused 500 ng (16.7 g/kg) showed completely regressed alveoli with little milk expressed within the lumen compared to the control saline treated R4th, which showed full and distended alveoli and substantial milk engorgement (dark staining, lower panels of FIG. 14). Of the larger alveoli in glands infused with 500 ng (16.7 µg/kg) Poly (I:C), milk staining was weak and there was an accumulation of neutrophils compared to the saline control. Similar effects were observed in glands infused with 250 ng (8.3 µg/kg) Poly (I:C), albeit with less severe inflammatory effects. The 250 ng (8.3 µg/kg) dose was better tolerated by mice than 500 ng (16.7 µg/kg), with mice maintaining body weight and showed no signs of adverse effects of systemic inflammation. Thus, a dose of 50-250 ng (1.67-8.3 µg/kg) is sufficient to decrease milk production and induce precocious involution with no adverse side effects.

3.2.2 Poly (I:C) Intramammary Infusion Results in Lactation Shut Down that is Associated with Increased Phosphorylated Stat1 and Loss of Phosphorylated Stat5.

Figure 15:
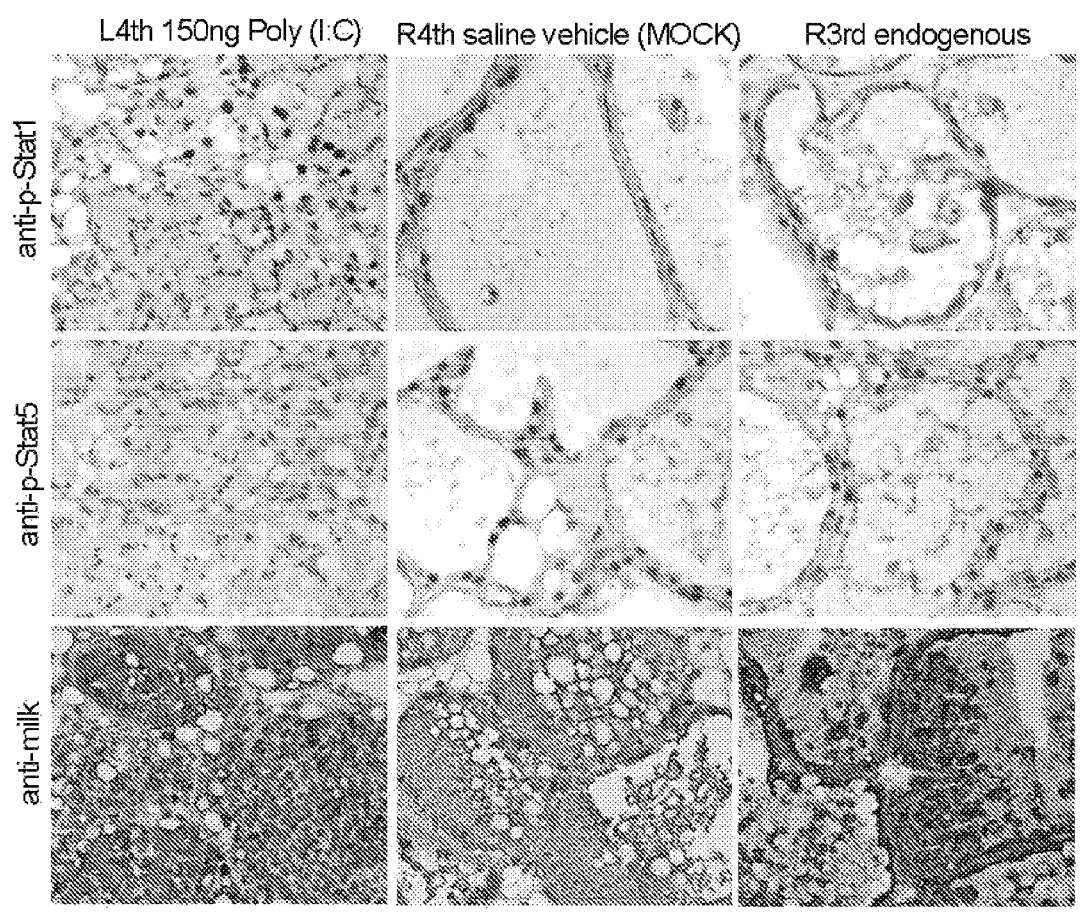
FIG. 15 illustrates that Poly (I:C) intramammary infusion results in increased phosphorylated Stat1 (p-Stat1), decreased phosphorylated Stat5 (p-Stat5), neutrophil accumulation, alveolar collapse and lactation failure. The photomicrographs depict DAB+ immunohistochemistry using antibodies raised against phosphorylated Stat1, phosphorylated Stat5 and mouse Milk in the region proximal the inguinal teat of mammary glands from mice injected with either Poly (I:C) (left (L) mammary gland) or vehicle control (right (R) mammary gland), collected at 48 hrs after injection and forced involution.

As is evident from FIG. 15, the left $4^{th}$ mammary glands showed focal regions of increased phosphorylated Stat1, loss of phosphorylated Stat5 and decreased milk accumulation compared to saline-infused right control mammary glands and endogenous R3rd mammary glands, demonstrating that Poly (I:C) treatment resulted in similar effects to activation of OAS2 caused by the I405N mutation.

Example 4. Intramammary Infusion of Poly (I:C) to Mice During Lactation

In this example, the inventors show that Poly (I:C) intramammary infusion causes no permanent defects in lactation competence of mice.

4.1 Methods

As robust effects with no obvious adverse systemic toxicities were observed in Example 3 when a 250 ng (8.3 µg/kg) dose of Poly (I:C) was administered, this dose was selected to test whether lactation could be rescued on a second pregnancy in Poly (I:C) treated mammary glands.

In this experiment, the left mammary glands of 10 dpp lactating mice were infused with 250 ng (8.3 µg/kg) Poly (I:C) (prepared as per Tables 3 and 4) with the right mammary glands treated with a saline control injection. At 24 hours after forced involution, successful Poly (I:C) intramammary infusion was visualized by observing the proximal area surrounding the 4th teat underneath the skin, which when compared to distal region of the same mammary gland lacked the white milk engorged area expected after forced weaning. Mice were kept alive and then allowed to recover for 2-3 weeks, re-mated and allowed to lactate for 6 days (6 days post partum, 6dpp). At 6dpp the mice were euthanised and mammary glands collected for histology.

Immunohistochemistry was performed on mammary glands collected at 6dpp according to the methods described in Example 2 and using a rabbit antibody against mouse milk (Accurate Chemical & Scientific Corporation, as described in Table 2). The $3^{rd}$ (axial) endogenous mammary glands were used as a control.

4.2 Results

Figure 16:
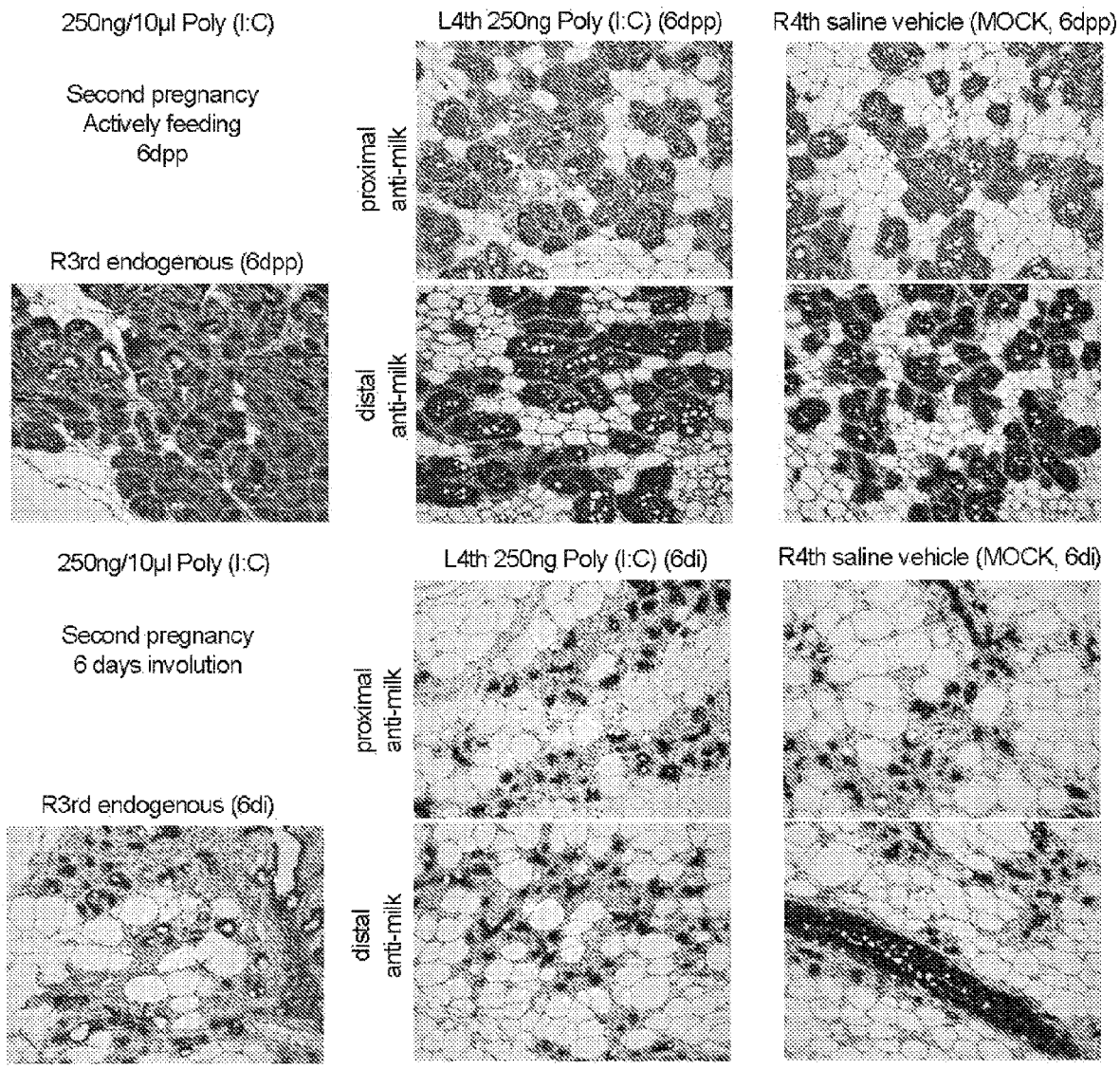
FIG. 16 illustrates that the effects of Poly (I:C) intramammary infusion on the first pregnancy are completely rescued on the second pregnancy. The photomicrographs depict the milk (dark brown staining) in the mammary glands proximal or distal to the inguinal teat in mammary gland from mice injected with either Poly (I:C) (left (L) mammary gland) or vehicle control (right (R) mammary gland), collected at either 6 days of lactation (6dpp, top panels) or 6 days of involution (6di, lower panels).

Immunohistochemistry using the antibody to mouse milk showed that both the proximal and distal regions of the mammary glands infused with Poly (I:C) on the first pregnancy lactated normally on the second pregnancy and showed no defects in alveolar structure nor milk production when compared to saline controls or uninjected R3rd endogenous controls (FIG. 16 top panels). Pups that were attached to these dams also increased in weight as normal. No alveolar milk engorgement was observed as expected from mice actively lactating.

Likewise, when pups were removed at birth rather than at 6 days of lactation, mammary involution occurred normally and was not altered by the Poly (I:C) treatment during the first lactation.

In summary these data suggest that Poly (I:C) infusion results in an inflammatory response resulting in lactation shut down and precocious involution, which has no long term effect on lactation competence on subsequent pregnancies.

Example 5. Udder Infusion of Poly I:C in Holstein Dairy Cows

In this example, the inventors show that infusion of poly I:C into the udders of Holstein dairy cows causes transient immunostimulation and suppressed lactation without undesirable side effects.

5.1 Rationale

A proof-of-concept (POC) study was performed in lactating Holstein dairy cows using intramammary (udder) infusion of polyinosinic-polycytidylic acid potassium salt, poly I:C. The purpose of this study was to identify a safe dose range for intramammary infusion of poly I:C and to provide evidence of immunostimulation and lactation inhibition after poly I:C intramammary infusion in a dairy cow model. More specifically, the study was designed to:

1. Identify the minimum dosage of poly I:C required to achieve mammary gland immunostimulation—indicated by an increase in somatic cell count (SCC) in milk.
2. Identify possible undesirable systemic side effects caused by immunostimulation with poly I:C at varying dosages.
3. Determine effects (if any) of immunostimulation at varying dosages of poly I:C on milk production rate (MPR).
4. Determine any pathological changes in the mammary glands, such as clinical inflammation, caused by effective dosages of poly I:C.
5. Determine whether SCC and/or MPR recover(s) to typical levels following poly I:C infusion.

Somatic cell count (SCC) is a measurement of immune cells in milk, expressed as a number of cells in one millilitre of milk. Somatic cells are primarily white blood cells (leukocytes, 98%), along with a smaller number (2%) of milk-producing cells that are shed from the udder tissue. SCC levels are lowest during peak lactation and higher in colostrum and late lactation. In colostrum, SCC (leukocytes) leak through into milk because the epithelial boundaries (tight junctions) are very leaky. Late in lactation milk production is generally declining, which causes an apparent increase in SCC due to the concentrating effect of lower milk secretion.

Whereas Examples 1 to 4 demonstrate that intramammary infusion of poly I:C is able to activate the intramammary immune response and suppress lactation in a rodent model, this experiment was designed to evaluate whether intramammary infusion of poly I:C in dairy cows would have the same effect.

5.2 Methods 5.2.1 Animal

Holstein dairy cows within a major university dairy herd were qualified based on a set of relevant health and production criteria. Late lactation cows (250-320 days-in-milk) were used in the study. The cows were multiparous and non-pregnant (open). Each cow had four functional quarters with undamaged teats at the beginning of the study. Production levels were equal or greater than 35 lbs milk/day (equal or greater than 15.4 litres milk/day) production on a twice daily milking schedule. The cows included in the study were also chosen on the basis that they had a history of stable milk production (i.e. low variance day-to-day) in their current lactation.

Housing and feeding protocols followed standard procedures for a late-lactation open (non-pregnant) dairy cows at the University of Wisconsin.

5.2.2 Protocol

The following protocol was performed prior to each treatment:
   Data on half-udder milk production was collected for days −7 through 0.
   CMT (California Mastitis Test) was performed on each udder cow-side at each milking.
   Microbial culture analysis on any milk sample with a positive CMT.
   Milk samples from AM milking on Day −2 and −1 were collected and frozen.
   Baseline SCCs were determined at −48 h and −24 h relative to infusions.
   Baseline core temperatures were determined at −48 h and −24 h relative to infusions.

On each day of treatment the cows were given control and experimental infusions using the following protocol:
   Intramammary infusion by teat cannula of poly I:C diluted in 10 ml vehicle (normal saline) per quarter in two quarters only.
   Given following AM milking on Day 0.
   Contralateral two quarters received vehicle-only.
   Antiseptic teat dip following treatment.
   Milk sample from AM milking collected and frozen.
   Each quarter was massaged after infusion to distribute infusion.

The following protocol was used for data collection after treatment:
   Twice daily milking continued and half-udder milk production rates (kg/hr) were calculated.
   Milk samples were collected and frozen at 0, 12, 24, 36, 48, 72, and 96 hour post-infusion.
   Core temperature was recorded during the PM milking on Day 0 through Day 7 (relative to each treatment).
   Observed changes in behaviour (agitation, vocalisation, recumbency) were recorded at each milking.
   Udders were observed at each milking for signs of soreness, edema, or inflammation to monitor udder health.
   SCC was measured in milk samples at 0, 12, 24, 36, 48, 72 and 96 hours post-infusion.
      Microbiological analysis was performed for any animal with elevated SCC (positive CMT).
      The immunostimulatory effect of poly I:C was predicted to cause treatment-dependent increases in SCC.
      Treatment-dependent SCC response was predicted to occur without any infection (sterile mastitis).

The above protocol was repeated and the next infusion was given following the AM milking on day 11 (ten day wash out):
   $1^{st}$ dosing cycle=0.1 µg in 10 ml vehicle.
   $2^{nd}$ dosing cycle=1 µg in 10 ml vehicle.
   $3^{rd}$ dosing cycle=10 µg in 10 ml vehicle.
   $4^{th}$ dosing cycle=0.1 mg in 10 ml vehicle.
   $5^{th}$ dosing cycle=1 mg in 10 ml vehicle.
   $6^{th}$ dosing cycle=10 mg in 10 ml vehicle.

5.3. Results 5.3.1 Cow Health

Cows were healthy throughout the study. Specifically, body temperatures and respiration rates remained normal in all cows. There were also no abnormal or indicative behaviour changes observed in the cows.

5.3.2 Udder Health

The mammary glands (udders) were healthy within the normal range of typical occurrences. One cow stepped on one of her teats and the damage resulted in cessation of lactation in that quarter. However, there were no occurrences of edema, inflammation, soreness, or other gross pathological indications in the udders. Because each cow received the agent (poly I:C) in two quarters and the control infusion in the other two quarters, it was possible to document that there were no differences in udder health between the treated quarters and the control quarters in any of the individual cows.

Intramammary infection occurrences were low during the study (6 infected quarters, all *staphylococcus*). All of these infections occurred early in the study, and none of the cases were associated with the Poly I:C treatment. This rate of intramammary infection was within the range normally expected.

5.3.3 Induction of Immune Reaction in Udders by Poly I:C

Figure 17:
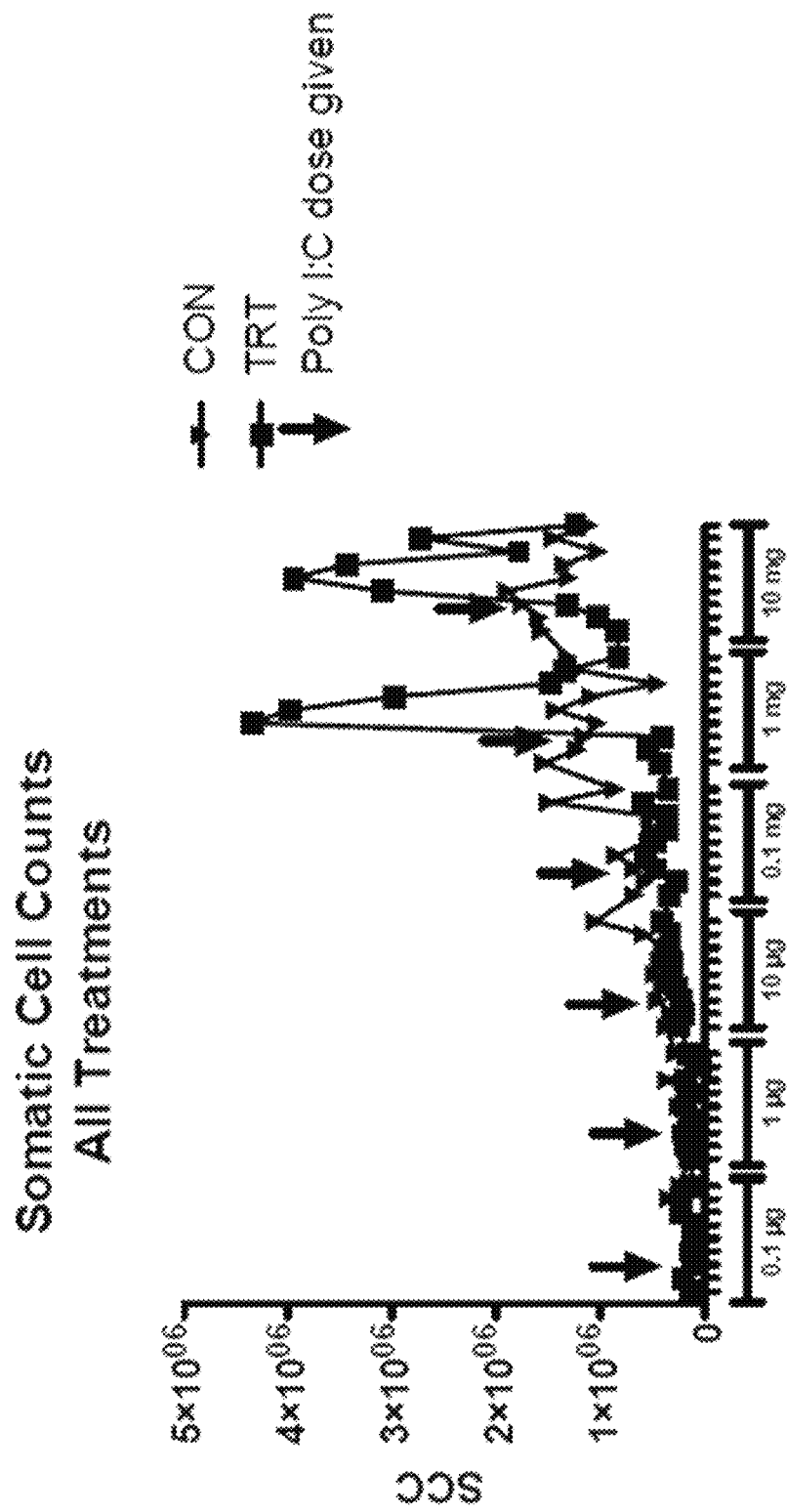
FIG. 17 illustrates the effect of intramammary infusion of poly I:C on somatic cell counts (SCC) in milk of Holstein dairy cows. Poly I:C was infused by teat cannula at the indicated dosages on the days marked by arrows. SCC in A.M. milk was measured the 2 days prior to infusion and the 4 days following infusion.

Infusion of poly I:C into dairy cow udders caused a dose-dependent local immune response in the treated udder quarters, as measured by SCC (FIG. 17). The effect of each dosage was analysed by 2-way ANOVA (time X treatment), at a statistical significance of $P<0.05$, with Bonferroni post-test to compare individual times. There were overall highly significant effects for both treatment ($P<0.01$) and time ($P<0.01$), and a significant interaction between treatment and time ($P<0.01$). At the two highest dosages (1 and 10 mg per quarter) SCC levels increased significantly at 12-36 hour in the poly I:C treated quarters of cows. SCC levels then declined to the control level by 96 hour (4 days) after the various treatments. There was no evidence of any crossover effects from infusion of poly I:C into the two untreated quarters. SCC levels in all udder quarters gradually increased because of the normal late lactation pattern. However, the control quarters did not show any SCC increase that mirrored the poly I:C-induced changes in the treated quarters.

5.3.4 Effects of Poly I:C on Milk Production Rate in Dairy Cows

Figure 18:
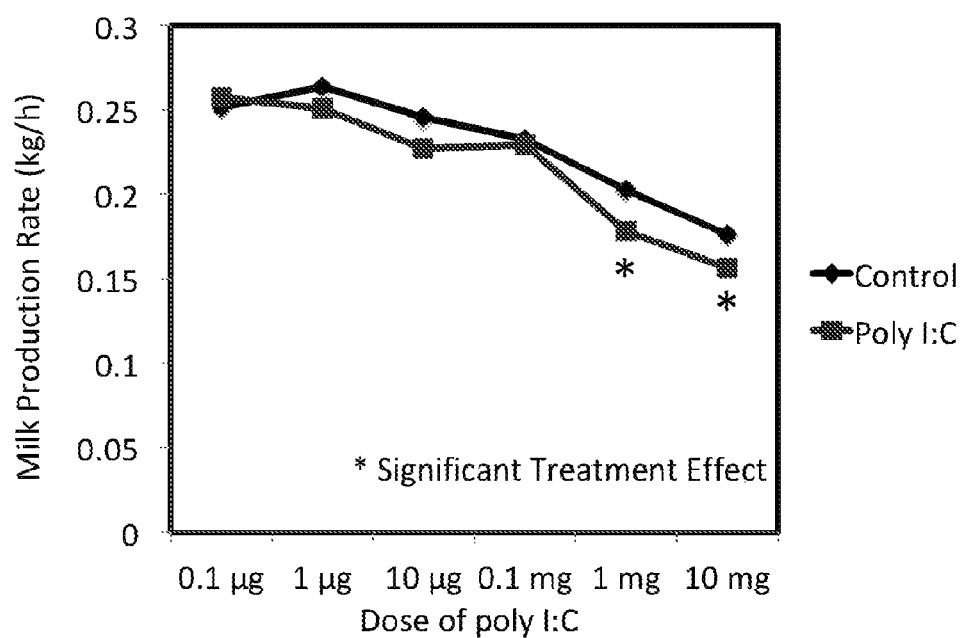
FIG. 18 illustrates the effect of poly I:C infusion into the udders of Holstein dairy cows on milk production rates. The data show a declining trend of late lactation MPR with additional inhibition of MPR caused by poly I:C infusions. There were highly significant treatment effects at the 5th and 6th treatment times (1 mg and 10 mg dosages respectively).

There were treatment-related decreases in milk production rates (MPR) in poly I:C-treated udder quarters at the two highest dosages of infusion (FIG. 18). Half-udder MPR for the control and poly I:C treated quarters was calculated for each cow during the post-treatment interval (96 hour post treatment) and analysed by 1-way ANOVA. There were highly significant treatment effects at the $5^{th}$ and $6^{th}$ treatment times (1 mg and 10 mg dosages respectively). There was an overall trend of declining MPR in all cows because of the normal pattern in which MPR decreases during late lactation. The effects of poly I:C were superimposed as an additional inhibition of MPR.

5.4 Conclusions

Several conclusions may be drawn from this study.
1. 1 mg per quarter was identified as the minimum dosage that caused an increased SCC in milk (indicative im ummunostimulation in the mammary gland).
2. There were no observable systemic side effects following infusions of poly I:C into dairy cow udders.
3. There were no observable changes in body temperature, respiratory rate, or behaviors in dairy cows following infusions of poly I:C into their udders.
4. MPR declined in late lactation, and poly I:C caused an additional inhibition of MPR at dosages of 1 and 10 mg per quarter.

5. There were no pathological effects on the udders related to poly I:C infusion at any of the dosages tested.
6. Within the dosage range tested, the SCC levels recovered to control levels by 4 days after poly I:C infusions. Because of the declining trend of MPR in late lactation, it was not possible to determine the extent of MPR recovery in this study.

In summary, the data in this example show that poly I:C can be infused into the udders of dairy cows and cause a local immune reaction that causes SCC levels to increase and MPR to decrease. The changes in mammary gland function caused by poly I:C were not associated with any negative side effects health of the udders or the whole body health of the cows.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

It is to be understood that any discussion of public documents, acts, materials, devices, articles or the like included herein is solely for the purpose of providing a context for the present invention. It is not to be taken as an admission that any or all of these matters were common general knowledge in the field relevant to the present invention as it existed before the priority date of any claim of this application.

The invention claimed is:

1. A method of reducing or shutting down lactation in a non-human mammalian subject not suffering from mastitis and in whom lactation needs to be reduced, said method comprising administering to the mammary gland of the subject by intramammary infusion an agent which activates the OAS2 signalling pathway or induces expression of OAS2 in the mammary gland of the subject, wherein the agent is a TLR agonist is (i) a double stranded RNA molecule selected from the group consisting of: polyinosinic-polycytidylic acid (Poly (I:C) or a derivative thereof selected from polyI:polyC(12)U and polyinosinic-polycytidylic acid stabilized with poly-L-lysine and carboxymethylcellulose (Poly-ICLC); and polyadenylic-polyuridylic acid (poly A:U), or (ii) a CpG dinucleotide (CpG-ODN), and wherein the agent is administered in an amount sufficient to reduce or shut down lactation in the non-human mammalian subject.

2. The method according to claim 1, wherein the agent which activates the OAS2 signalling pathway or induces expression of OAS2 in the mammary gland is Poly (I:C).

3. The method according to claim 1, wherein said method comprises:
administering a single dose of the agent to the non-human mammalian subject to thereby reduce or shut down lactation;
administering repeat doses of the agent until lactation is reduced or shut down; or
administering the agent to the non-human mammalian subject on a daily basis until lactation is reduced or shut down.

4. The method according to claim 1, wherein said method comprises:
administering repeat doses of the agent until lactation is reduced or shut down; and/or
administering the agent to the non-human mammalian subject on a daily basis until lactation is reduced or shut down.

5. The method according to claim 1, wherein reducing or shutting down lactation in the subject prevents mastitis in the non-human mammalian subject.

6. The method according to claim 5, wherein administering the agent which activates the OAS2 signalling pathway or induces expression of OAS2 in the mammary gland is sufficient to prevent mastitis in the non-human mammalian subject in the absence of an antimicrobial agent.

7. The method according to claim 1, wherein:
   the method does not comprise administering an antimicrobial agent to the non-human mammalian subject; and/or
   the method consists essentially of administering to the mammary gland of the non-human mammalian subject by intramammary infusion the agent which activates the OAS2 signalling pathway or induces expression of OAS2 in the mammary gland of the subject.

8. The method according to claim 1, wherein the method further comprises administering to the non-human mammalian subject:
   an antimicrobial agent to prevent microbial infection in the mammary gland of the subject; and/or
   a further agent which shuts down or reduces lactation.

9. The method according to claim 1, wherein the non-human mammalian subject is:
   a livestock animal;
   a ruminant livestock animal used in the production of milk for human consumption; and/or
   a dairy cow.

10. A method of preventing mastitis in a non-human mammalian subject which is lactating and not suffering from mastistis, comprising reducing or shutting down lactation in the non-human mammalian subject by performing a method according to claim 1.

* * * * *